(12) United States Patent
Choi et al.

(10) Patent No.: US 10,512,582 B2
(45) Date of Patent: Dec. 24, 2019

(54) SUPPORTING MODULE AND MOTION ASSISTANCE APPARATUS INCLUDING THE SAME

(71) Applicant: Samsung Electronics Co., Ltd., Suwon-si, Gyeonggi-do (KR)

(72) Inventors: Byungjune Choi, Gunpo-si (KR); Youn Baek Lee, Yongin-si (KR); Jeonghun Kim, Hwaseong-si (KR); Se-Gon Roh, Suwon-si (KR); Minhyung Lee, Anyang-si (KR); Jongwon Lee, Uiwang-si (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1294 days.

(21) Appl. No.: 14/682,614

(22) Filed: Apr. 9, 2015

(65) Prior Publication Data

US 2016/0151227 A1 Jun. 2, 2016

(30) Foreign Application Priority Data

Dec. 1, 2014 (KR) .................. 10-2014-0169501

(51) Int. Cl.
*A61H 3/00* (2006.01)
*A61F 2/60* (2006.01)
(Continued)

(52) U.S. Cl.
CPC .............. *A61H 3/00* (2013.01); *A61F 2/60* (2013.01); *F16B 7/10* (2013.01); *F16B 7/22* (2013.01); *A61H 2003/007* (2013.01); *A61H 2201/1481* (2013.01); *A61H 2201/165* (2013.01); *A61H 2201/1628* (2013.01);
(Continued)

(58) Field of Classification Search
CPC .................. A61F 2/60; A61F 2002/607; A61F 2002/608; A61H 3/00; A61H 2003/007; A61H 2201/1481; A61H 2201/1628; A61H 2201/165; A61H 2201/1664; A61H 2201/1669; F16B 7/10; F16B 7/22; F16M 11/046; Y10T 403/32229; Y10T 403/32483; Y10T 403/32524;
(Continued)

(56) References Cited

U.S. PATENT DOCUMENTS 6,796,537 B1 * 9/2004 Lin ........................ F16M 11/30
                                                                248/127
7,301,759 B2 * 11/2007 Hsiung ................ H05K 5/0234
                                                                403/329

(Continued)

FOREIGN PATENT DOCUMENTS

JP          4093912 B2      6/2008
JP      2012-187385 A      10/2012
(Continued)

*Primary Examiner* — Josh Skroupa
(74) *Attorney, Agent, or Firm* — Harness, Dickey and Pierce, P.L.C.

(57) ABSTRACT

A supporting module and a motion assistance apparatus including the same, the supporting module including a supporting frame including a sliding guide, a sliding joint configured to slide along the sliding guide, and an elastic module provided in the supporting frame, and configured to provide an elastic force to the sliding joint, are provided.

17 Claims, 27 Drawing Sheets

(51) Int. Cl.
 *F16B 7/10* (2006.01)
 *F16B 7/22* (2006.01)
(52) U.S. Cl.
 CPC ............... *A61H 2201/1664* (2013.01); *A61H 2201/1671* (2013.01); *Y10T 403/32229* (2015.01); *Y10T 403/608* (2015.01)
(58) Field of Classification Search
 CPC ............... Y10T 403/598; Y10T 403/60; Y10T 403/606; Y10T 403/608
 USPC ... 403/80, 109.3, 109.8, 324, 326, 329, 330, 403/379.1
 See application file for complete search history.

(56) References Cited

U.S. PATENT DOCUMENTS

| | | | | |
|---|---|---|---|---|
| 7,591,401 | B2 * | 9/2009 | Sandler | A45F 3/14 224/201 |
| 8,405,959 | B2 * | 3/2013 | Lee | F16M 11/046 248/125.2 |
| 8,409,119 | B2 | 4/2013 | Shimizu et al. | |
| 8,708,941 | B2 * | 4/2014 | Paaske | A61F 5/0193 602/16 |
| 9,289,317 | B2 * | 3/2016 | Goldfarb | A61F 2/60 |
| 9,554,960 | B2 * | 1/2017 | Kamon | A61H 3/00 |
| 9,662,262 | B2 * | 5/2017 | Hollander | A61H 3/00 |
| 2016/0158087 | A1 * | 6/2016 | Huang | A61F 2/60 623/30 |
| 2016/0331624 | A1 * | 11/2016 | Sankai | A61H 3/00 |
| 2016/0331625 | A1 * | 11/2016 | Sankai | A61H 3/00 |

FOREIGN PATENT DOCUMENTS

| | | |
|---|---|---|
| JP | 2013-090881 A | 5/2013 |
| JP | 5313609 B2 | 10/2013 |
| KR | 10-0716597 B1 | 5/2007 |
| KR | 10-20120047664 A | 5/2012 |
| KR | 101142240 B1 | 5/2012 |
| KR | 10-1226926 B1 | 1/2013 |

* cited by examiner

SUPPORTING MODULE AND MOTION ASSISTANCE APPARATUS INCLUDING THE SAME

CROSS-REFERENCE TO RELATED APPLICATION

This application claims the priority benefit of Korean Patent Application No. 10-2014-0169501, filed on Dec. 1, 2014, in the Korean Intellectual Property Office, the entire contents of which are incorporated herein by reference in its entirety.

BACKGROUND

1. Field

Example embodiments relate to a supporting module and/or a motion assistance apparatus including the same.

2. Description of the Related Art

With the onset of rapidly aging societies, an increasing number of people may experience inconvenience and/or agony from joint problems, and, therefore, there is interest in motion assistance apparatuses that may assist patients having joint problems with walking. The motion assistance apparatuses may include active joint structures including hydraulic systems and/or driving motors to drive each joint portion to improve muscular strength of legs of the users.

SUMMARY

Some example embodiments relate to a supporting module.

In some example embodiments, the supporting module may include a supporting frame including a sliding guide, a sliding joint configured to slide along the sliding guide, and an elastic module provided in the supporting frame, and configured to provide an elastic force to the sliding joint.

The elastic module may include a constant force spring configured to provide a constant force to the sliding joint, irrespective of a change in a position of the sliding joint.

The elastic module may be configured to provide an elastic force to the sliding joint so that the sliding joint is positioned at a center of the sliding guide.

The elastic module may include a first elastic member and a second elastic member configured to apply forces to the sliding joint in opposite directions, in a state in which another external force is not applied to the sliding joint.

The supporting module may further include a slider slidingly provided in the sliding guide. The elastic module may connect the supporting frame to the slider, and the sliding joint may be connected to the slider.

The sliding joint may include a joint body configured to be coupled to or separated from the supporting frame, and a hanging portion provided on one side of the joint body, and on which the slider is configured to be hung.

The slider may be hung on the hanging portion when the joint body is coupled to the supporting frame, and the slider may be separated from the hanging portion when the joint body is separated from the supporting frame.

Other example embodiments relate to a supporting module.

In some example embodiments, the supporting module may include a supporting frame including a sliding guide, a slider slidingly provided in the sliding guide, and a sliding joint configured to be coupled to or separated from the slider based on a relative moving direction with respect to the supporting frame.

The sliding joint may include a joint body configured to be inserted into or drawn out from the supporting frame, and a hanging portion provided on one side of the joint body, and on which the slider is configured to be hung.

The slider may be hung on the hanging portion when the joint body is inserted into the supporting frame by a length greater than or equal to a first set length.

The supporting frame may further include a temporary fixing portion formed to be recessed from the sliding guide, and configured to temporarily fix the slider.

The sliding joint may further include a hanging guide provided on another side of the joint body, and configured to guide the slider from the temporary fixing portion to the sliding guide.

The temporary fixing portion may be formed to be inclined from the sliding guide toward an insertion direction of the sliding joint, and the hanging guide may be formed to be inclined to have a steeper slope than the temporary fixing portion.

The slider may be separated from the hanging portion when the joint boy is drawn out from the supporting frame by a length greater than or equal to a second set length.

The supporting frame may further include a separation guide configured to extend from the sliding guide, and guide the slider to be separated from the hanging portion.

The separation guide may extend to be inclined from the sliding guide toward a drawing-out direction of the sliding joint.

The supporting frame may further include a sliding space configured to have a larger cross-sectional area than the sliding joint, and into which the sliding joint is configured to be inserted, and a gap preventing member disposed between an inner wall of the supporting frame and the sliding joint.

An end portion of the sliding space may be configured to have a smaller cross-sectional area than a central portion thereof, and the gap preventing member may include a fixing portion configured be fixed to the sliding joint, and a rib configured to protrude from the fixing portion, and be in contact with the end portion of the sliding space.

The supporting module may further include a separation preventing member provided in one of the supporting frame and the sliding joint, and configured to restrict a maximum length by which the sliding joint is to be drawn out from the supporting frame.

The sliding joint may include a sliding body having a plurality of joints.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
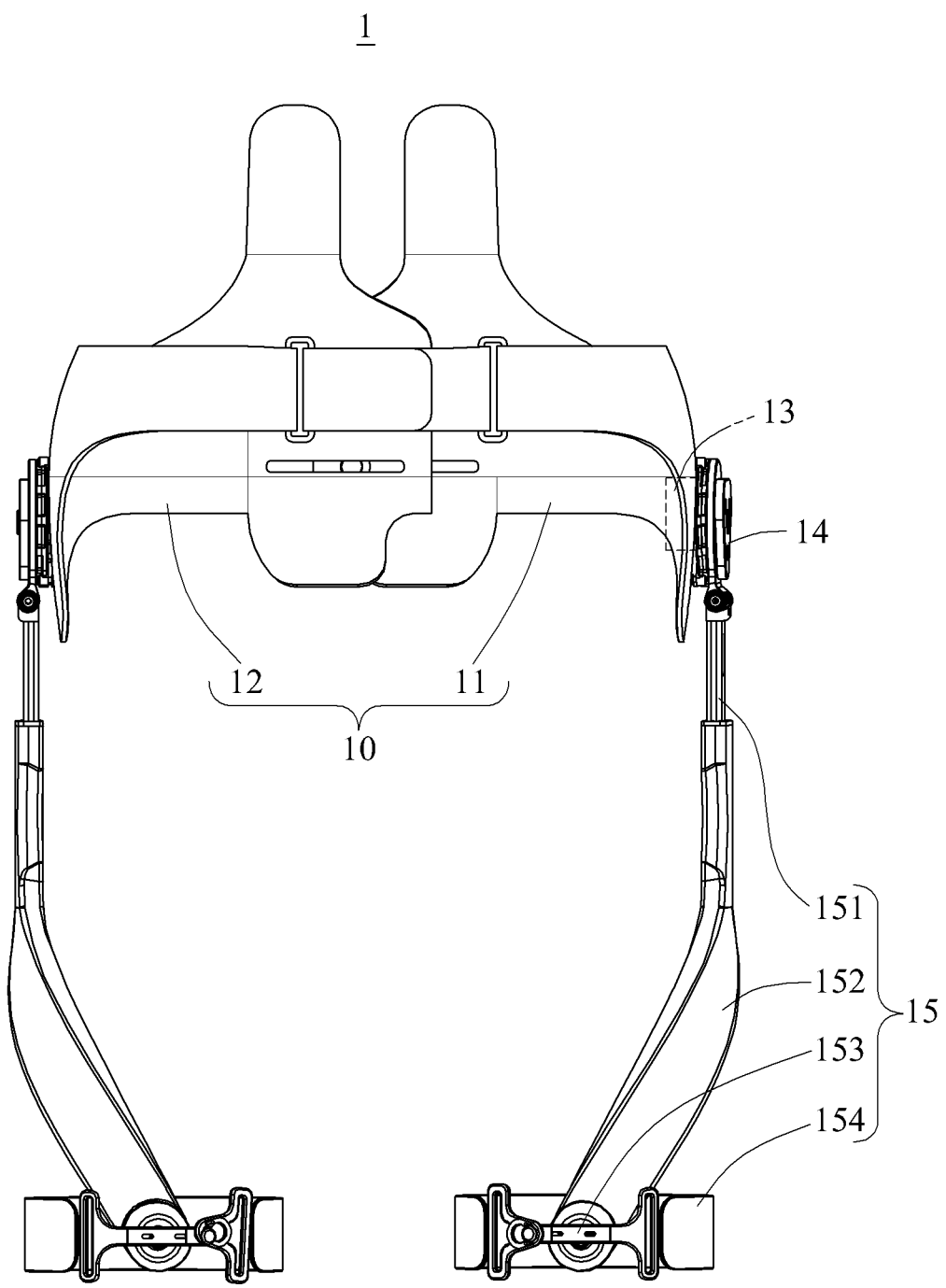
FIG. 1 is a front view of a motion assistance apparatus according to example embodiments.

Hereinafter, some example embodiments will be described in detail with reference to the accompanying drawings. Regarding the reference numerals assigned to the elements in the drawings, it should be noted that like elements will be designated by like reference numerals, wherever possible, even though they are shown in different drawings. Also, in the description of the example embodiments, detailed description of well-known related structures or functions may be omitted.

It should be understood, however, that there is no intent to limit this disclosure to the particular example embodiments disclosed. On the contrary, the example embodiments are to cover all modifications, equivalents, and alternatives falling within the scope of example embodiments.

In addition, terms such as first, second, A, B, (a), (b), and the like may be used herein to describe components. Each of these terminologies is not used to define an essence, order or sequence of a corresponding component but is used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
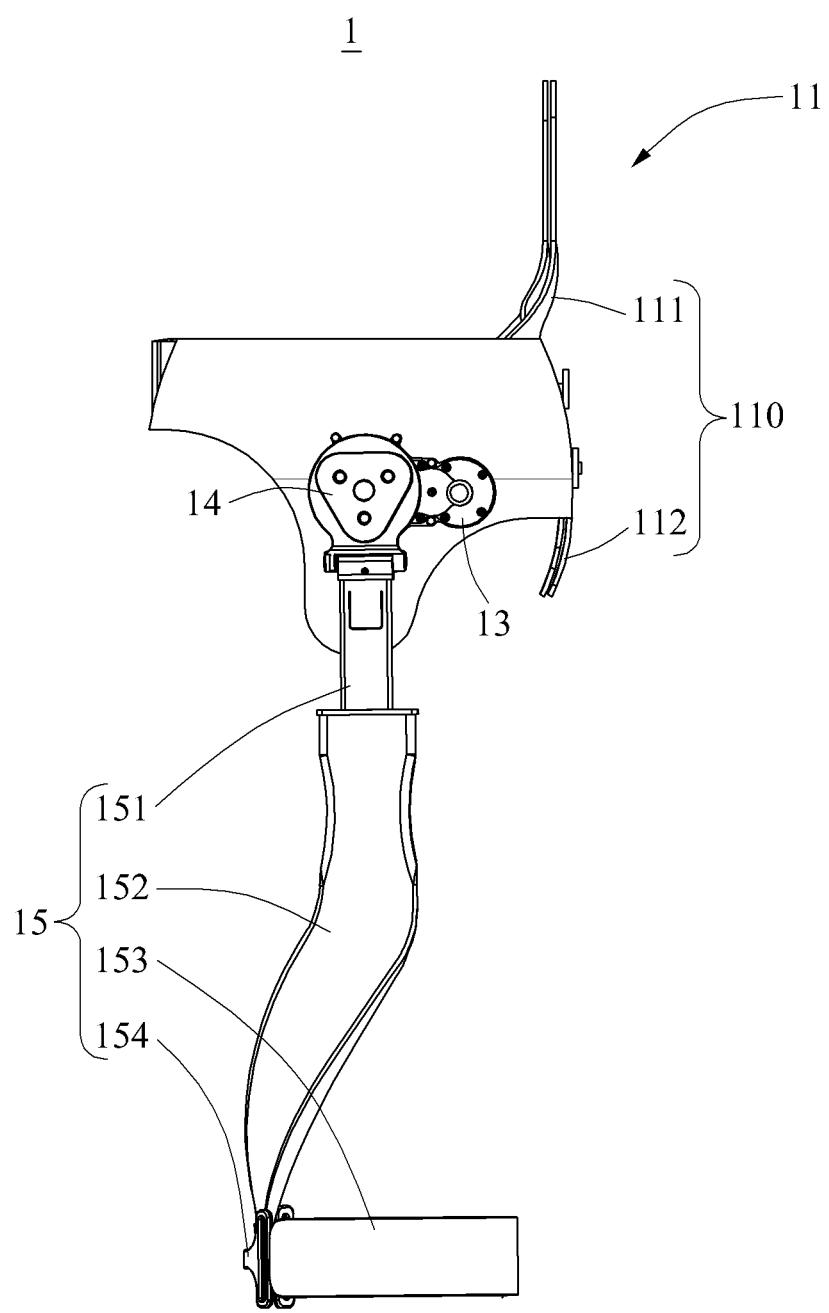
FIG. 2 is a side view of a motion assistance apparatus according to example embodiments.

FIG. 1 is a front view of a motion assistance apparatus 1 according to example embodiments, and FIG. 2 is a side view of the motion assistance apparatus 1 according to example embodiments.

Referring to FIGS. 1 and 2, the motion assistance apparatus 1 may be worn by a user and may assist the user with performing motion.

In some example embodiments, the user may be a human, an animal, or a robot. However, example embodiments are not limited thereto. Although FIG. 1 illustrates a case in which the motion assistance apparatus 1 assists a motion of a thigh of the user, the motion assistance apparatus 1 may also assist a motion of another part of an upper body, for example a hand, an upper arm, and a lower arm of the user, or a motion of another part of a lower body, for example, a foot, and a calf of the user. The motion assistance apparatus 1 may assist a motion of a part of the user. Hereinafter, a case in which the motion assistance apparatus 1 assists a motion of a thigh of a human will be described.

The motion assistance apparatus 1 may include a fixing module 10, a driving module 13, a rotary joint 14, and a supporting module 15.

The fixing module 10 may be attached to the user, and may cover an outer surface of the user. For example, the fixing module 10 may be attached to one side of a waist of the user, and may include a curved surface corresponding to a contact portion of the user. The fixing module 10 may include a first side frame 11 disposed on one side of the user, and a second side frame 12 disposed on another side of the user. The first side frame 11 and the second side frame 12 may be detachable from each other. A distance between the first side frame 11 and the second side frame 12 may be adjusted to be suitable for a body condition of the user.

As illustrated in FIG. 2, the first side frame 11 may include a first supporting member 110 configured to support one side of the user. The first supporting member 110 may include a first upper supporting member 111 configured to support an upper side of the user, and a first lower supporting member 112 configured to support a lower side of the user. Although not illustrated in detail, similar to the first side frame 11, the second side frame 12 may include a second upper supporting member and a second lower supporting member.

The driving module 13 may provide power to be transmitted to the rotary joint 14. For example, the driving module 13 may be disposed in a lateral direction of the rotary joint 14, in detail, such that a rotation axis of the driving module 13 may be spaced apart from a rotation axis of the rotary joint 14. In this example, when compared to a case in which the driving module 13 and the rotary joint 14 share a rotation axis, a protruding height from the user may relatively decrease. Dissimilar to the drawings, the driving module 13 may be disposed to be spaced apart from the rotary joint 14 much more. In this example, a power transmitting module may be additionally provided to transmit power from the driving module 13 to the rotary joint 14. The power transmitting module may be a rotary body such as, for example, a gear, or a longitudinal member such as, for example, a wire, a cable, a string, a rubber band, a spring, a belt, and a chain.

The rotary joint 14 may rotate using power received from the driving module 13. The rotary joint 14 may assist a motion of a joint portion of the user. The rotary joint 14 may be disposed on one side of the fixing module 10 at a position corresponding to the joint portion of the user. For example, the rotary joint 14 may be disposed on one side of a hip joint of the user. One side of the rotary joint 14 may be connected to the driving module 13, and another side of the rotary joint 14 may be connected to the supporting module 15.

The supporting module 15 may support a portion of the user, and assist a motion of the portion of the user. The supporting module 15 may be configured to rotate using torque of the rotary joint 14. The supporting module 15 may include a hinge connection structure, thereby being coupled to the rotary joint 14. In this example, by a hinge axis of the hinge connection structure and a rotation axis of the rotary joint 14, the supporting module 15 may perform a two degree of freedom (DOF) motion with respect to the fixing module 10. The supporting module 15 may include a sliding joint 151, a supporting frame 152, an applying member 153, and a supporting band 154.

The sliding joint 151 may connect the rotary joint 14 to the supporting frame 152, and rotate using torque of the rotary joint 14. The sliding joint 151 may be provided to slide along the supporting frame 152.

The supporting frame 152 may transmit force to a part of the user. One end portion of the supporting frame 152 may be rotatably connected to the sliding joint 151, and another end portion of the supporting frame 152 may be connected to the supporting band 154 to transmit force to a portion of the user. For example, the supporting frame 152 may push or pull a thigh of the user. The supporting frame 152 may extend and be bent in a longitudinal direction of the thigh of the user to cover at least a portion of a circumference of the thigh of the user. The one end portion of the supporting frame 152 may be disposed on a side surface of the thigh of the user, and the other end portion of the supporting frame 152 may be disposed on a front surface of the thigh of the user. In detail, a surface on the side of the one end portion of the supporting frame 152 may be orthogonal to a surface on the side of the other end portion of the supporting frame 152.

The applying member 153 may be connected to the other end portion of the supporting frame 152 to apply force to a portion of the user. For example, the applying member 153 may be disposed along the front surface of the thigh of the user, or in a circumferential direction of the thigh of the user to push or pull the high of the user. The applying member 153 may include a curved surface corresponding to the thigh of the user, and configured to extend from the other end portion of the supporting frame 152 toward both sides of the supporting frame 152.

The supporting band 154 may be connected to one side of the applying member 153. For example, the supporting band 154 may be disposed to cover a circumference of at least a portion of the thigh of the user, thereby preventing separation between the high of the user and the supporting frame 152.

Figure 3:
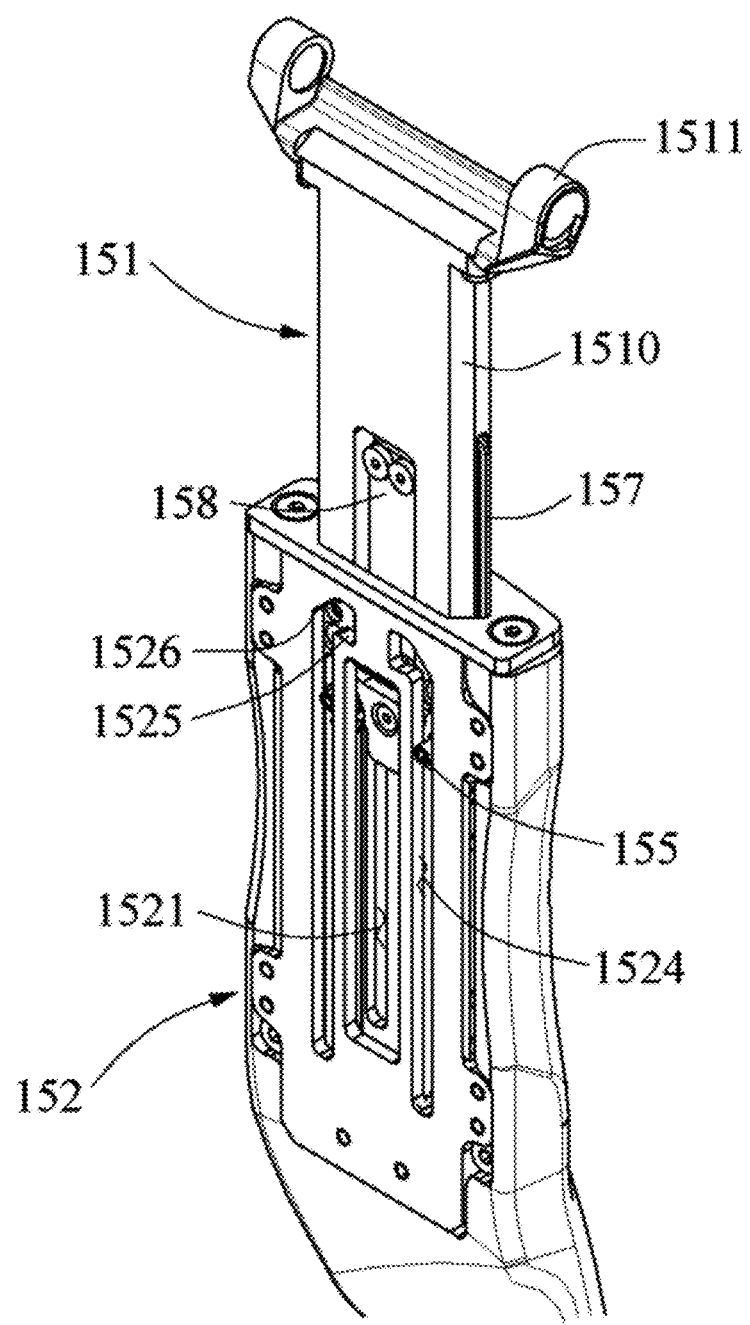
FIG. 3 is a partial perspective view of a supporting module according to example embodiments.
Figure 4:
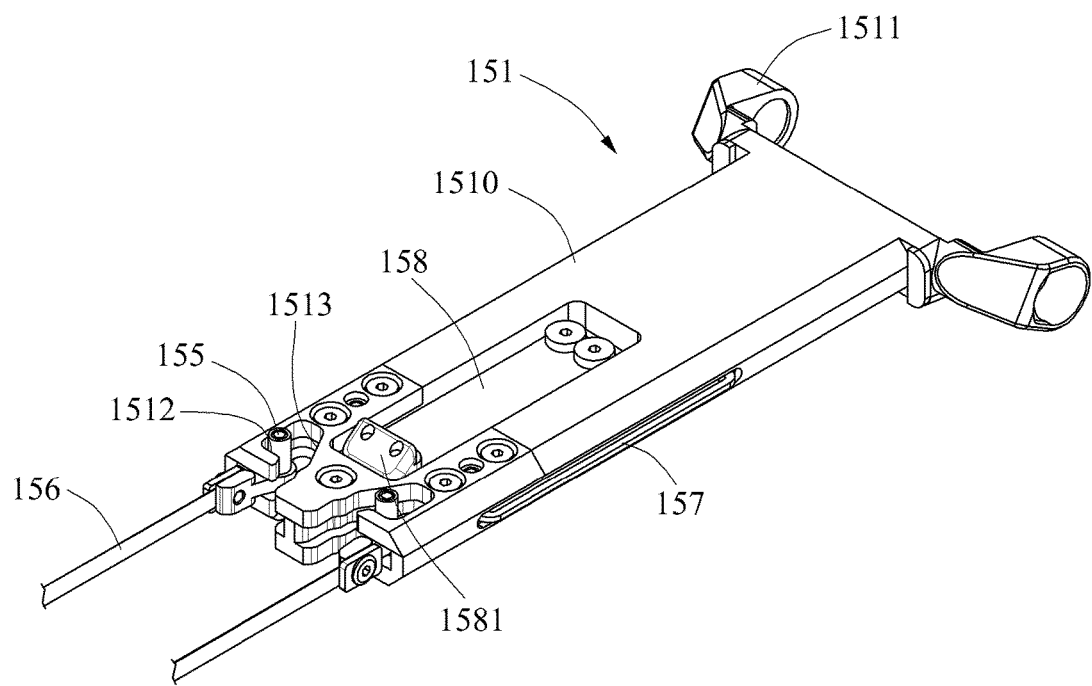
FIG. 4 is a perspective view of a sliding joint according to example embodiments.
Figure 5:
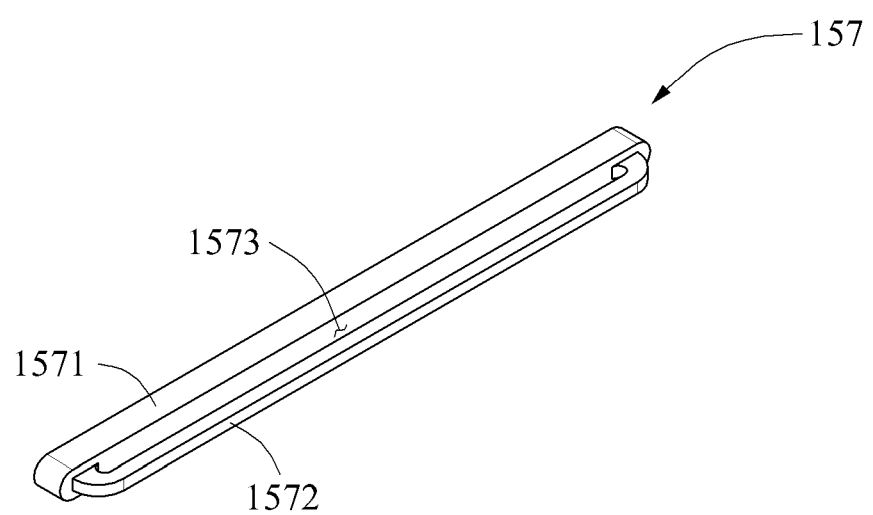
FIG. 5 is a perspective view of a gap preventing member according to example embodiments.
Figure 6A:
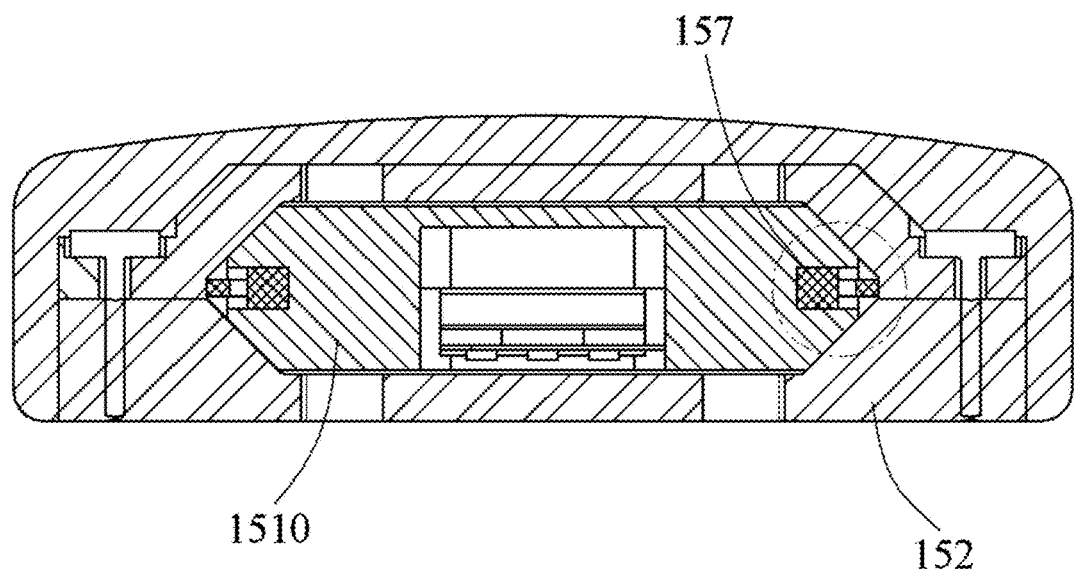
FIGS. 6A and 6B is a cross-sectional view of a supporting module according to example embodiments.
Figure 6B:
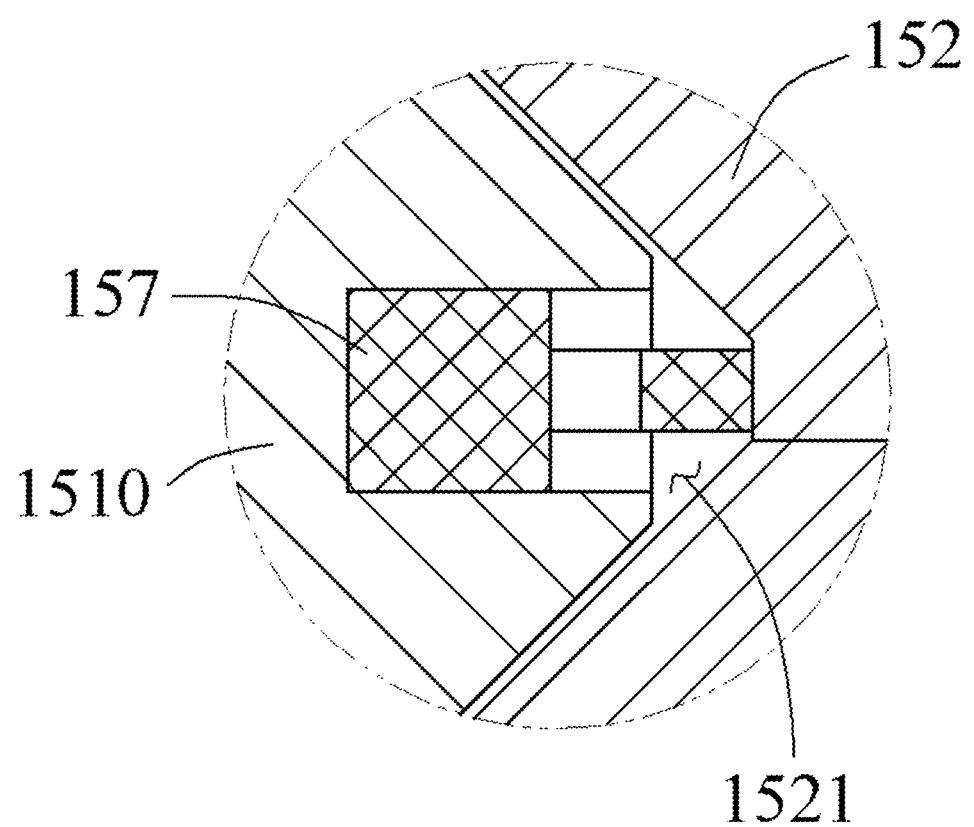
Figure 7:
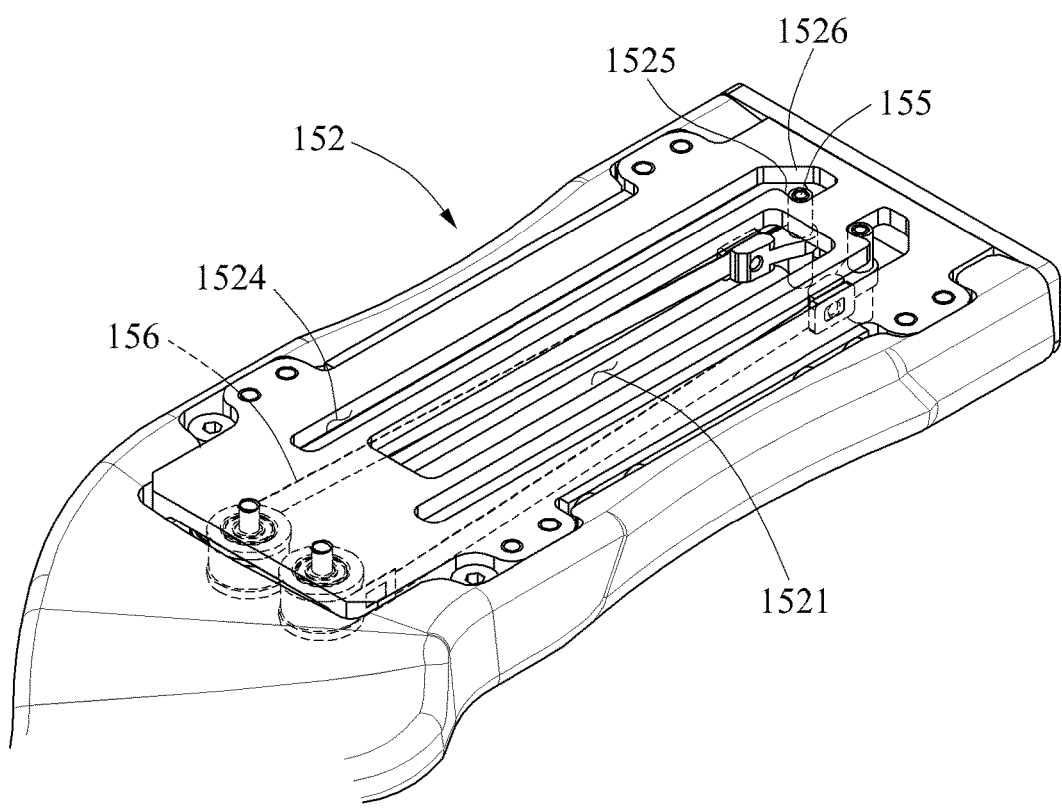
FIG. 7 is a partial perspective view of a supporting frame according to example embodiments.
Figure 8A:
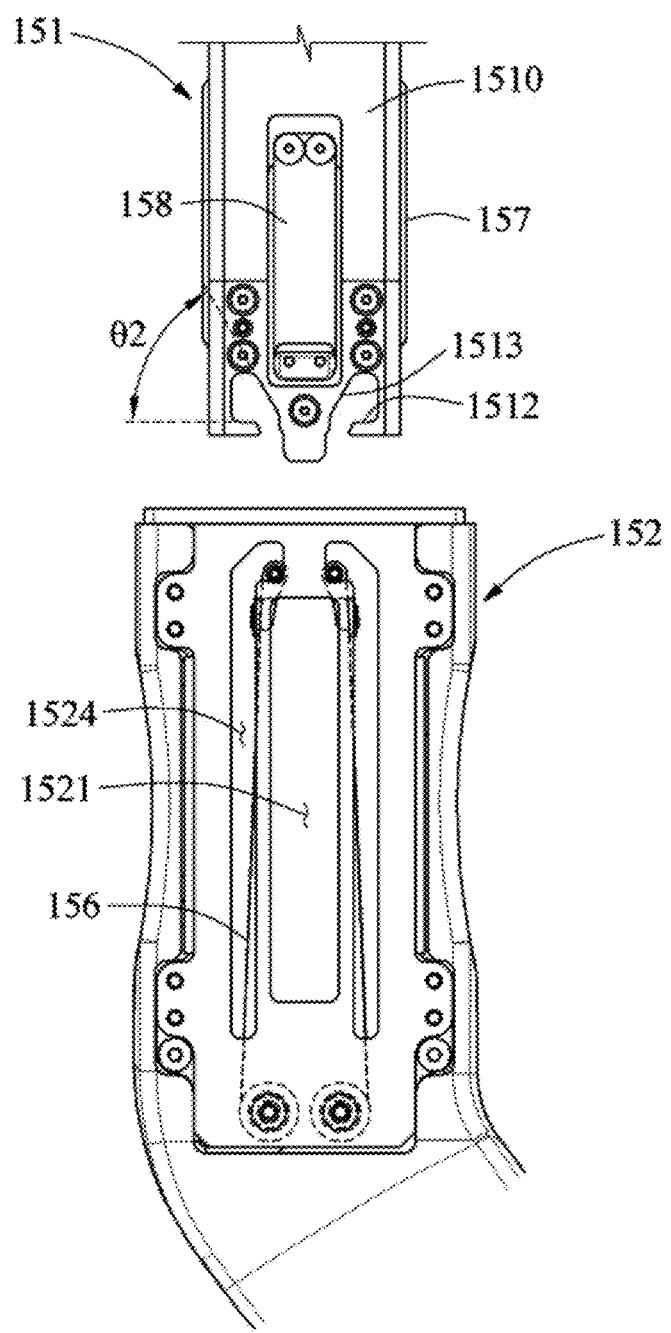
FIGS. 8A and 8B is a view illustrating a sliding joint and a supporting frame being separated from each other according to example embodiments.
Figure 8B:
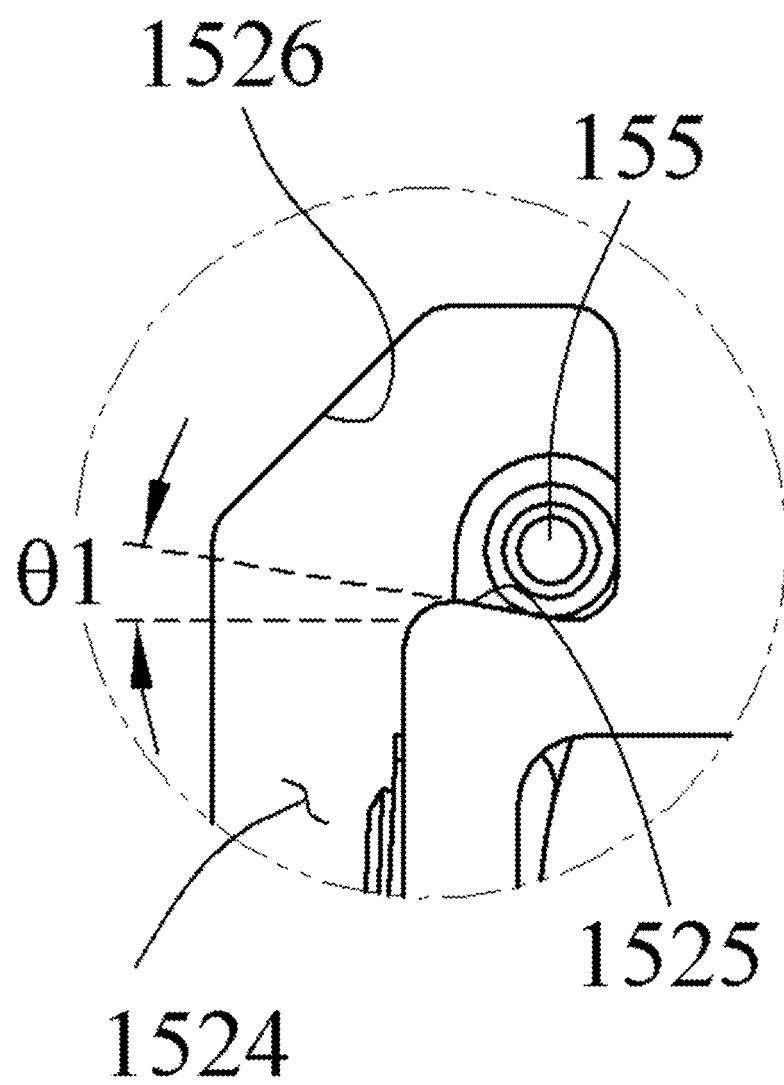

FIG. 3 is a partial perspective view of the supporting module 15 according to example embodiments, FIG. 4 is a perspective view of the sliding joint 151 according to example embodiments, FIG. 5 is a perspective view of a gap preventing member 157 according to example embodiments, FIGS. 6A and 6B is a cross-sectional view of the supporting module 15 according to example embodiments, FIG. 7 is a partial perspective view of the supporting frame 152 according to example embodiments, and FIGS. 8A and 8B is a view illustrating the sliding joint 151 and the supporting frame 152 being separated from each other according to example embodiments.

Referring to FIGS. 3 through 8, the supporting module 15 may include the sliding joint 151, the supporting frame 152, a slider 155, an elastic module 156, the gap preventing member 157, and a separation preventing member 158.

The sliding joint 151 may slide with respect to the supporting frame 152. The sliding joint 151 may be detachable from the supporting frame 152. The sliding joint 151 may include a joint body 1510 configured to form an outer shape, a hinge 1511 configured to be rotatably coupled to the rotary joint 14 of FIG. 2, a hanging portion 1512, and a hanging guide 1513.

The slider 155 may be hung on the hanging portion 1512. For example, the hanging portion 1512 may protrude from an end portion of a side surface of the joint body 1510 toward an inner side. The hanging portion 1512 may have a loop shape that is bent from an outer side of the joint body 1510 toward an inner side.

The hanging guide 1513 may guide the slider 155 to the hanging portion 1512. The hanging guide 1513 may be disposed to be spaced apart from the hanging portion 1512 such that the slider 155 may be inserted into a space formed between the hanging portion 1512 and the hanging guide 1513. The hanging guide 1513 may be inclined upward in a direction of the hanging portion 1512, as illustrated in FIGS. 8A and 8B. In detail, the hanging guide 1513 may be inclined toward the hanging portion 1512 in a direction in which the sliding joint 151 is separated from the supporting frame 152.

The supporting frame 152 may be movably connected to the sliding joint 151. By relative motions of the supporting frame 152 and the sliding joint 151, a total length from the rotary joint 14 to the supporting band 154 may be variable. In this example, the supporting module 15 may perform a three DOF motion with respect to the fixing module 10. By the foregoing structure, a total length of the entire supporting module 15 may be adjusted to be suitable for a different length of a thigh of each user. The supporting frame 152 may include a sliding space 1521, a sliding guide 1524, a temporary fixing portion 1525, and a separation guide 1526.

The sliding joint 151 may be inserted into the sliding space 1521. The sliding space 1521 may be a space recessed from one surface of the supporting frame 152. The sliding space 1521 may have a larger cross-sectional area than the sliding joint 151.

The sliding guide 1524 may guide a movement of the slider 155. The sliding guide 1524 may be fat lied to communicate with the sliding space 1521. The sliding guide 1524 may be formed in a longitudinal direction of the supporting frame 152.

The temporary fixing portion 1525 may temporarily fix the slider 155. The temporary fixing portion 1525 may be recessed from the sliding guide 1524. The temporary fixing portion 1525 may be recessed toward an inner side, as illustrated in FIGS. 8A and 8B. The temporary fixing portion 1525 may overlap the hanging guide 1513, when viewed from a coupling direction of the sliding joint 151 and the supporting frame 152. The temporary fixing portion 1525 may be inclined downward in a direction of an end portion, as illustrated in FIGS. 6A and 6B. In detail, the temporary fixing portion 1525 may be inclined in a direction in which the sliding joint 151 is coupled to the supporting frame 152. By the foregoing structure, in a case in which an elastic force of the elastic module 156 is applied to the slider 155, the slider 155 may be stably received in the temporary fixing portion 1525. An angle θ1 of inclination of the temporary fixing portion 1525 may be smaller than an angle θ2 of inclination of the hanging guide 1513.

The separation guide 1526 may guide the slider 155 to the temporary fixing portion 1525. The separation guide 1526 may extend to be inclined from the sliding guide 1524. The separation guide 1526 may be inclined upward in a direction of an inner side, as illustrated in FIGS. 6A and 6B. In detail, the separation guide 1526 may be inclined toward the temporary fixing portion 1525 in a direction in which the sliding joint 151 is separated from the supporting frame 152.

The slider 155 may be slidingly provided in the sliding guide 1524. The slider 155 may function as a connecting member of the sliding joint 151 and the supporting frame 152. The slider 155 may be disposed in the sliding guide 1524 when the sliding joint 151 is coupled to the supporting frame 152, and may be disposed in the temporary fixing portion 1525 when the sliding joint 151 is separated from the supporting frame 152. The slider 155 may be provided in a form of a cylindrical pin.

The elastic module 156 may be provided in the supporting frame 152, and configured to provide an elastic force to the sliding joint 151. One side of the elastic module 156 may be connected to the supporting frame 152, and another side of the elastic module 156 may be connected to the slider 155. In an example, the elastic module 156 may include a constant force spring configured to provide a constant force to the sliding joint 151, irrespective of a change in a position of the sliding joint 151. In another example, the elastic module 156 may include a member including another elastic material such as a tensile spring, a compression spring, and a rubber band, for example. The elastic module 156 may provide an elastic force to the sliding joint 151 so that the sliding joint 151 may be disposed at a center of the sliding guide 1524. In detail, when an external force is not applied in a state in which the sliding joint 151 is coupled to the supporting frame 152, the sliding joint 151 may be positioned at the center of the sliding guide 1524.

Dissimilar to the drawings, in some example embodiments, the elastic module 156 may be connected directly to the joint body 1510. In this example, the slider 155, or the hanging portion 1512, the hanging guide 1513, the sliding guide 1524, the temporary fixing portion 1525, or the separation guide 1526 that interoperates with the slider 155 may be omitted.

The gap preventing member 157 may be disposed between an inner wall of the supporting frame 152 and the sliding joint 151, and prevent shakes of the sliding joint 151 in the sliding space 1521 of the supporting frame 152. For example, as shown in FIGS. 6A and 6B, the gap preventing member 157 may reduce a frictional force by reducing a contact area between the sliding joint 151 and the supporting frame 152. Hereinafter, a case in which the gap preventing member 157 is fixed to the sliding joint 151, and moves while being in contact with the inner wall of the supporting frame 152 will be described. As illustrated in FIG. 5, the gap preventing member 157 may include a fixing portion 1571, and a rib 1572, such that, a cushion space 1573 is provided therebetween.

The fixing portion 1571 may be inserted into and fixed to an inner portion of the supporting frame 152.

The rib 1572 may protrude from the fixing portion 1571, and be in contact with an end portion of the sliding space 1521. Both contact portions may include different materials. In an example, one of the rib 1572 and the inner wall of the supporting frame 152 may be formed of metal, and the other may be formed of plastic. In another example, both the rib 1572 and the inner wall of the supporting frame 152 may be formed of metal, for example, an aluminum material, and one of the rib 1572 and the inner wall of the supporting frame 152 may include a coating layer including different materials, for example, a teflon coating layer.

The cushion space 1573 may be a space formed between the fixing portion 1571 and the rib 1572. The rib 1572 may be elastically deformed by the cushion space 1573. In an example, the cushion space 1573 may be omitted, and the rib 1572 may be formed of a flexible material.

The separation preventing member 158 may restrict a maximum length by which the sliding joint 151 is to be drawn out from the supporting frame 152. The separation preventing member 158 may be provided in one of the supporting frame 152 and the sliding joint 151. For example, as shown in FIG. 4, the separation preventing member 158 may be provided on one side of the sliding joint 151. In this example, the separation preventing member 158 may include a hook 1581 having a cross-sectional area decreasing in a direction in which the sliding joint 151 is coupled to the supporting frame 152. The separation preventing member 158 may be elastic. An operation of the separation preventing member 158 will be described later with reference to FIGS. 12A through 12C.

Figure 9A:
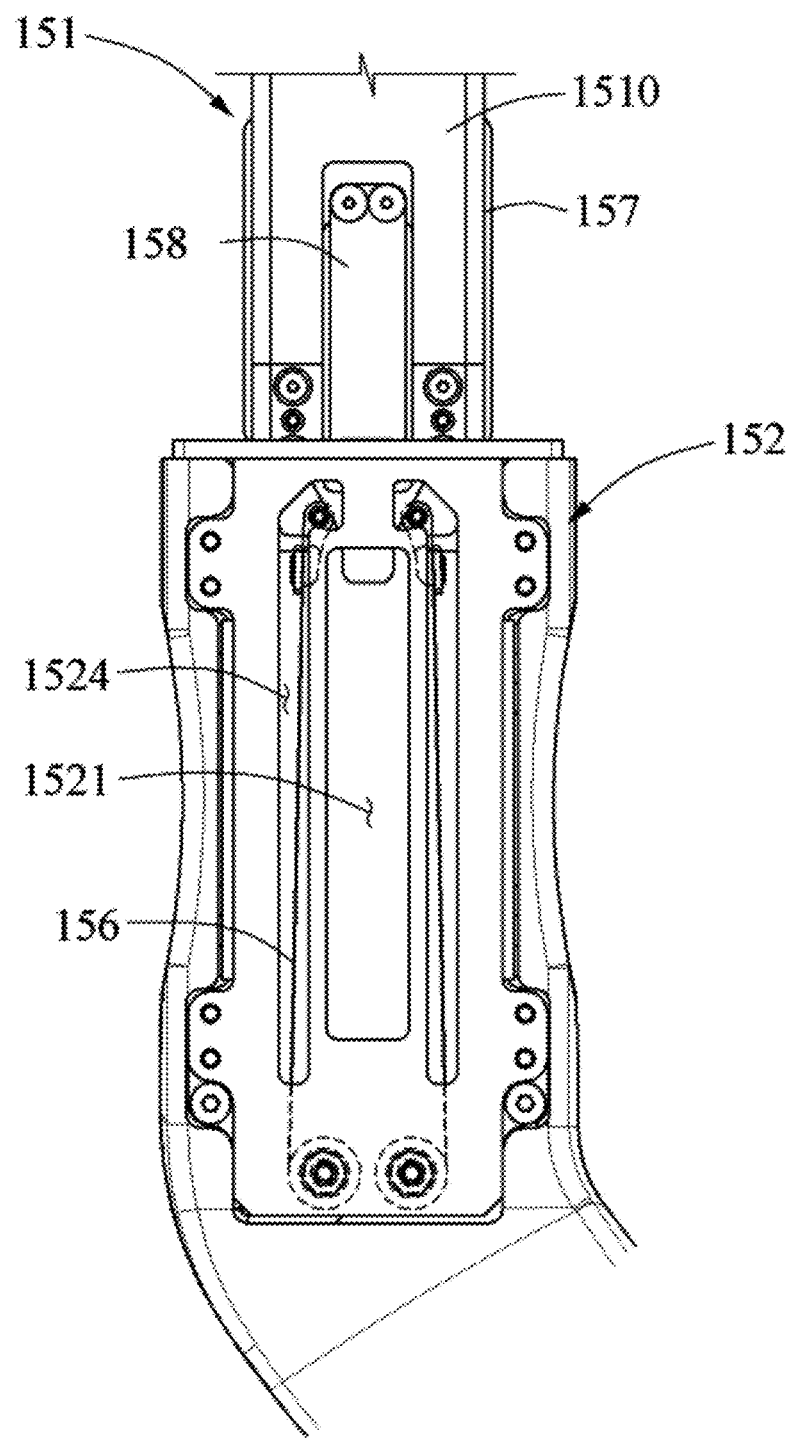
FIGS. 9A and 9B is a view illustrating a process of coupling a sliding joint to a supporting frame according to example embodiments.
Figure 9B:
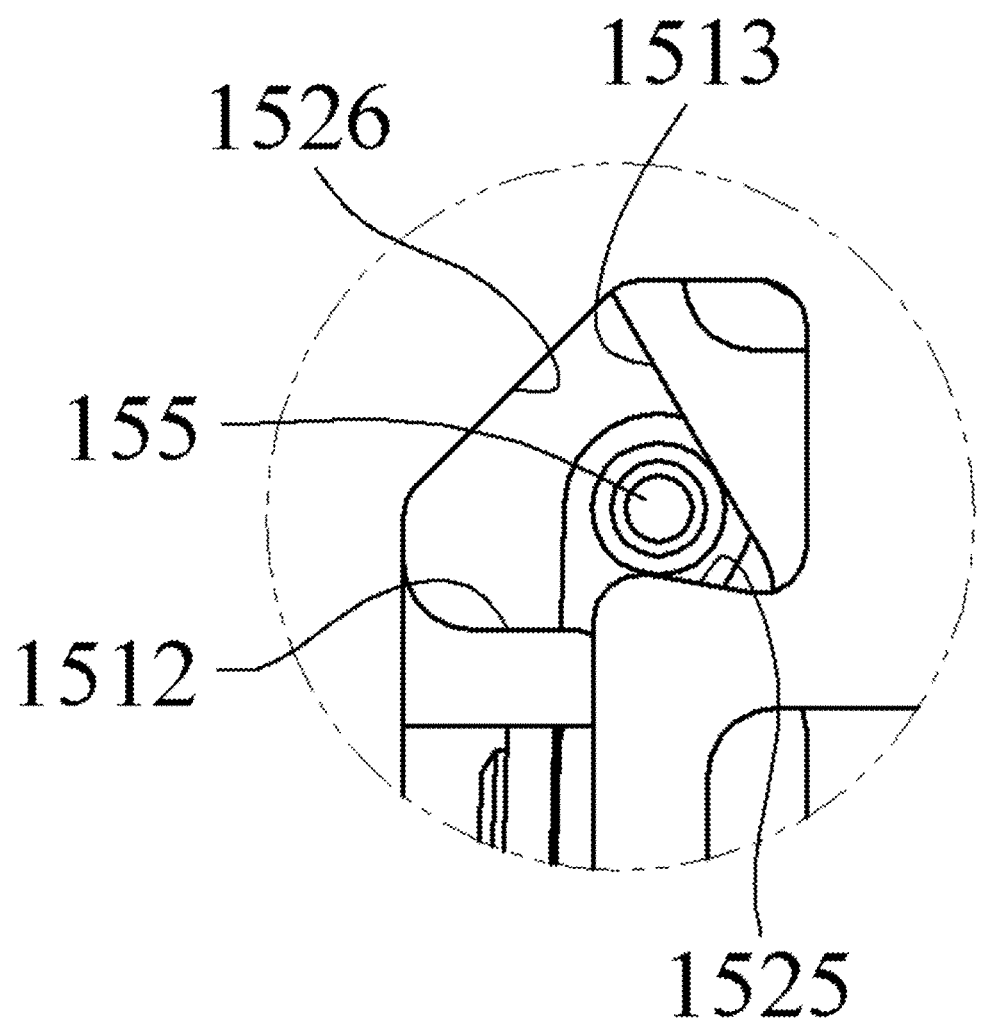
Figure 10:
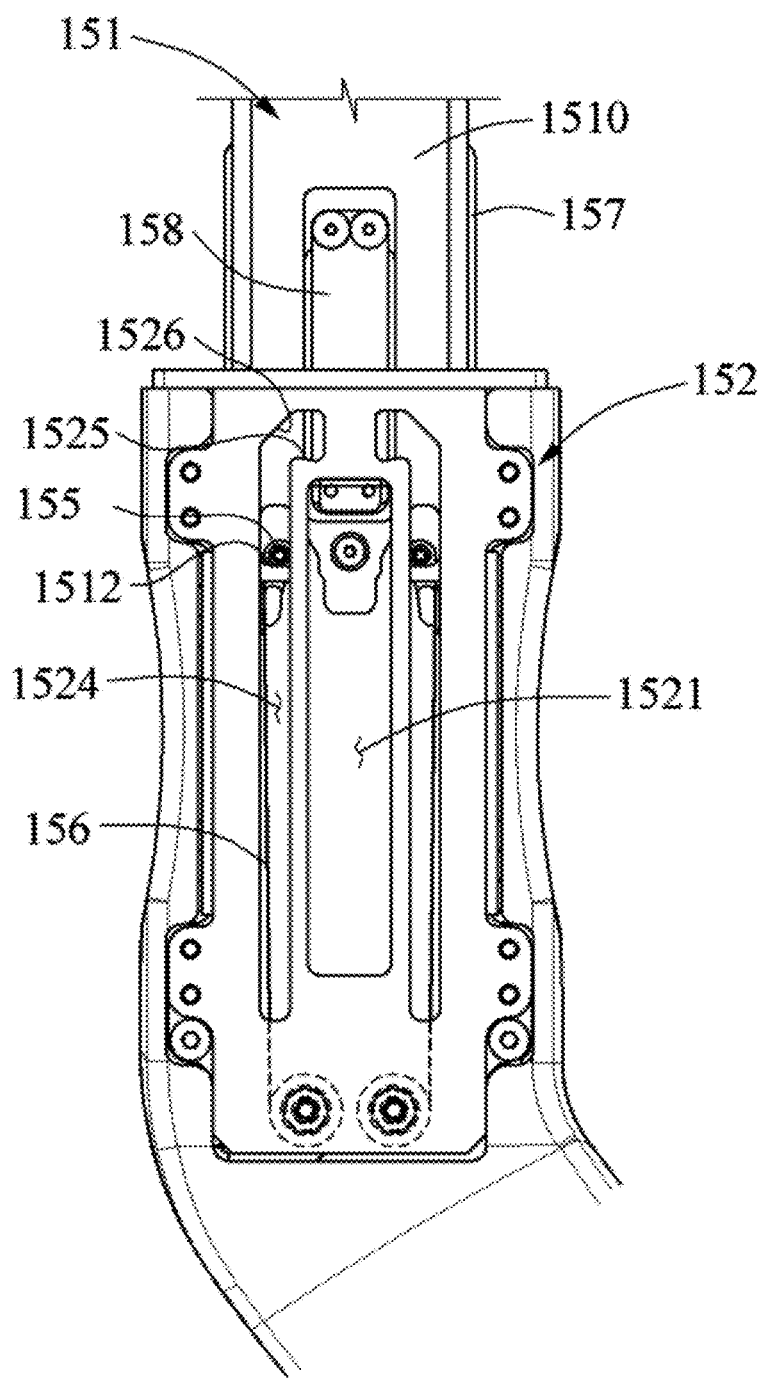
FIG. 10 is a view illustrating a sliding joint and a supporting frame being coupled to each other according to example embodiments.
Figure 11A:
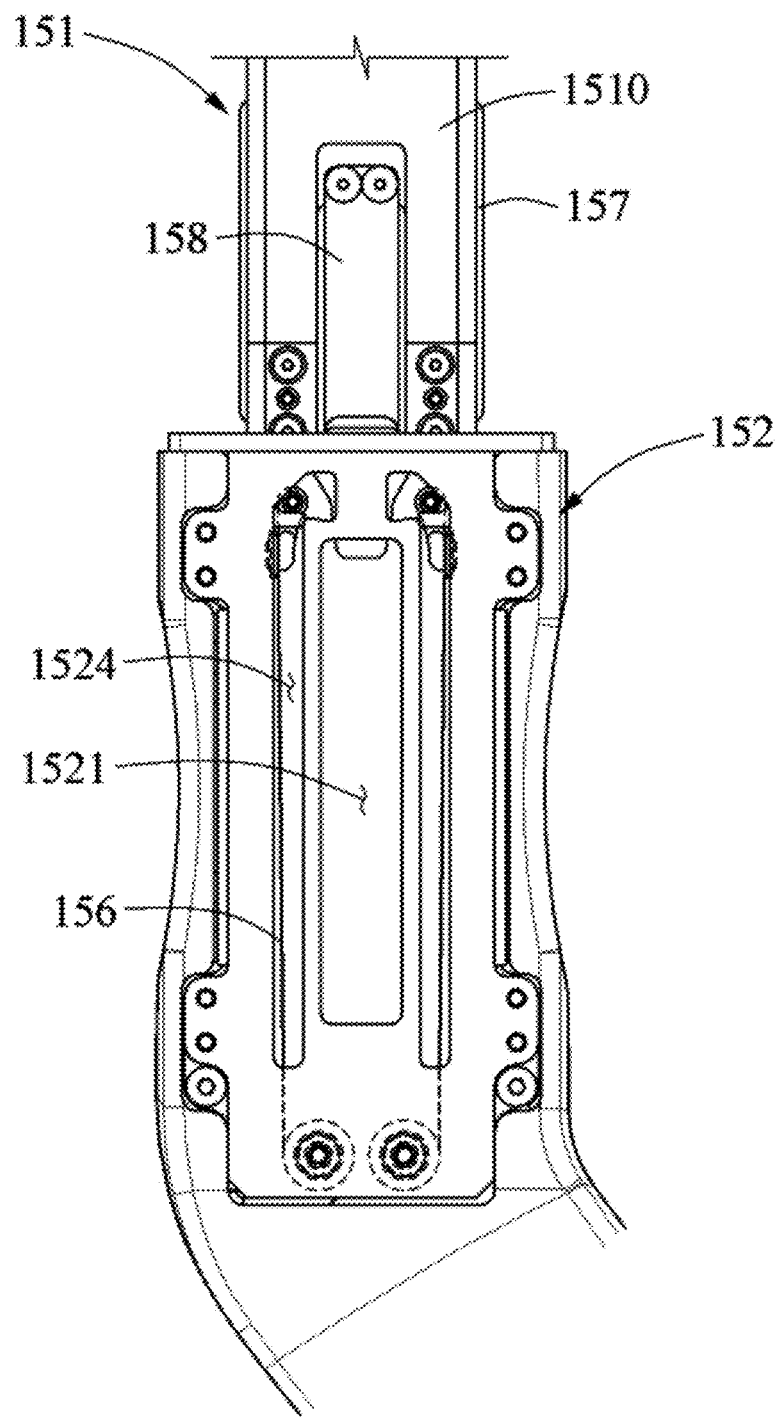
FIGS. 11A and 11B is a view illustrating a process of separating a sliding joint from a supporting frame according to example embodiments.
Figure 11B:
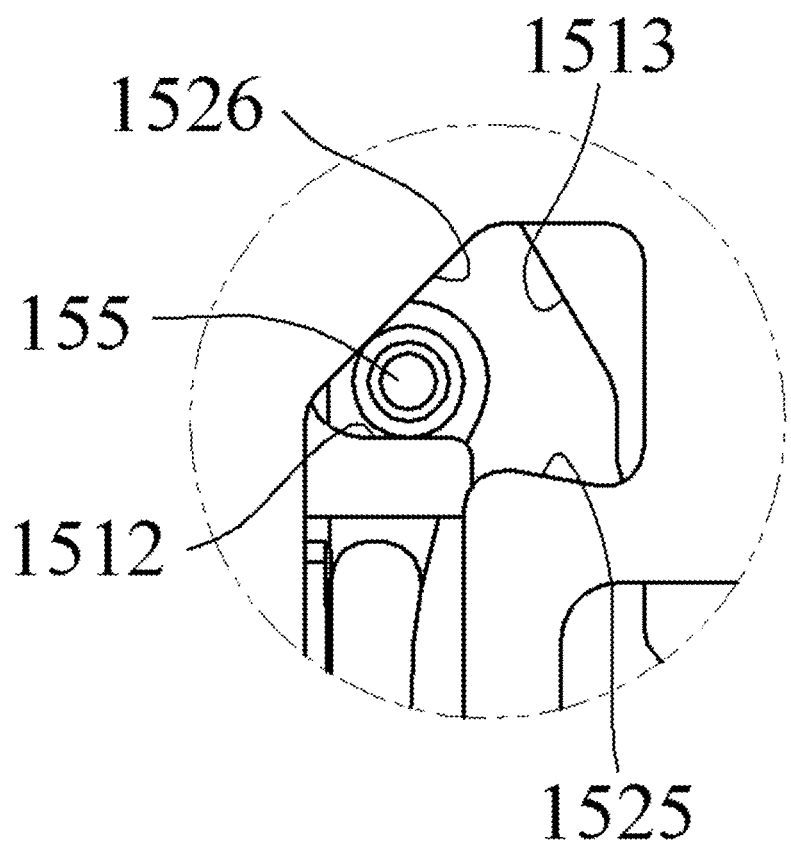

FIGS. 9A and 9B is a view illustrating a process of coupling the sliding joint 151 to the supporting frame 152 according to example embodiments, FIG. 10 is a view illustrating the sliding joint 151 and the supporting frame 152 being coupled to each other according to example embodiments, and FIGS. 11A and 11B is a view illustrating a process of separating the sliding joint 151 from the supporting frame 152 according to example embodiments.

Referring to FIGS. 8 through 11, the supporting module 15 of FIGS. 8A and 8B may be referred to as being in a "separation state" or "a coupling readiness state".

In the coupling readiness state as shown in FIGS. 8A and 8B, the sliding joint 151 may be inserted into the sliding space 1521 by a length greater than or equal to a desired (or, alternatively, a predetermined) uniform length, for example, a first set length, as shown in FIGS. 9A and 9B.

The hanging guide 1513 may push the slider 155 to be drawn out from the temporary fixing portion 1525 toward the sliding guide 1524. As shown in FIG. 10, the slider 155 may be guided toward the sliding guide 1524, and hung on the hanging portion 1512. Through the foregoing process, only by inserting the sliding joint 151 into the sliding space 1521, the sliding joint 151 and the supporting frame 152 may be coupled to each other by the slider 155 and the elastic module 156.

By the foregoing structure, in a state in which the fixing module 10 of FIG. 1 is attached to a waist of the user, and the supporting band 154 of FIG. 1 is attached to a thigh of the user, the sliding joint 151 and the supporting frame 152 may slide with respect to each other. Thus, although the rotary joint 14 of FIG. 1 is not positioned exactly at a hip joint of the user, a rotation axis of the hip joint and a rotation axis of the rotary joint 14 mismatch due to an adduction or abduction of the thigh of the user, or a portion of physical conditions of the user changes, the sliding joint 151 and the supporting frame 152 may appropriately slide, whereby the entire supporting module 15 of FIG. 1 may be in a state suitable for a lower body of the user. In summary, although a rotation direction of the rotary joint 14 does not match that of the hip joint of the user, a suitable assistance force may be applied to the supporting module 15.

In a state in which the sliding joint 151 is coupled to the supporting frame 152 as shown in FIG. 10, the sliding joint 151 may be moved by a length greater than or equal to a desired (or, alternatively, a predetermined) uniform length, for example, a second set length, in a direction in which the sliding joint 151 is separated from the supporting frame 152. In this example, the slider 155 may be moved upward by the hanging portion 1512, as shown in FIGS. 11A and 11B. The slider 155 may be guided along the separation guide 1526, thereby being separated from the hanging portion 1512. Consequently, the slider 155 may be separated from the hanging portion 1512, and hung on the temporary fixing portion 1525, as shown in FIGS. 8A and 8B. Through the foregoing process, only by separating the sliding joint 151 from the supporting frame 152, the slider 155 may be hung on the temporary fixing portion 1525. In detail, only by separating the sliding joint 151 from the supporting frame 152, the sliding joint 151 and the supporting frame 152 may be in the coupling readiness state as shown in FIGS. 8A and 8B.

Figure 12A:
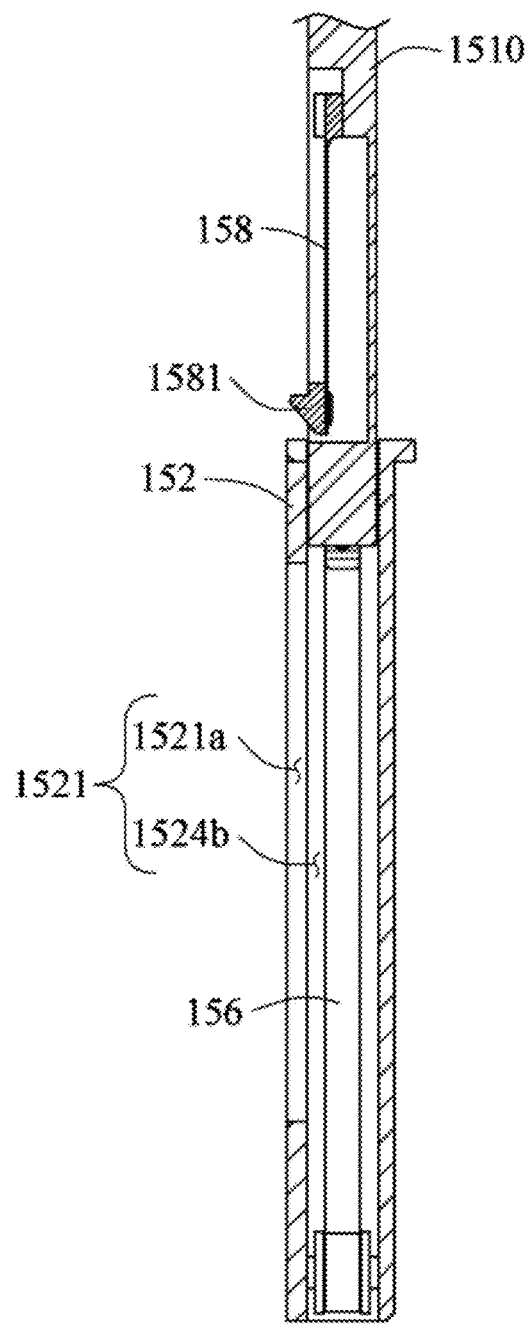
FIGS. 12A through 12C are cross-sectional views of a supporting module illustrating an operation of a separation preventing member according to example embodiments.
Figure 12B:
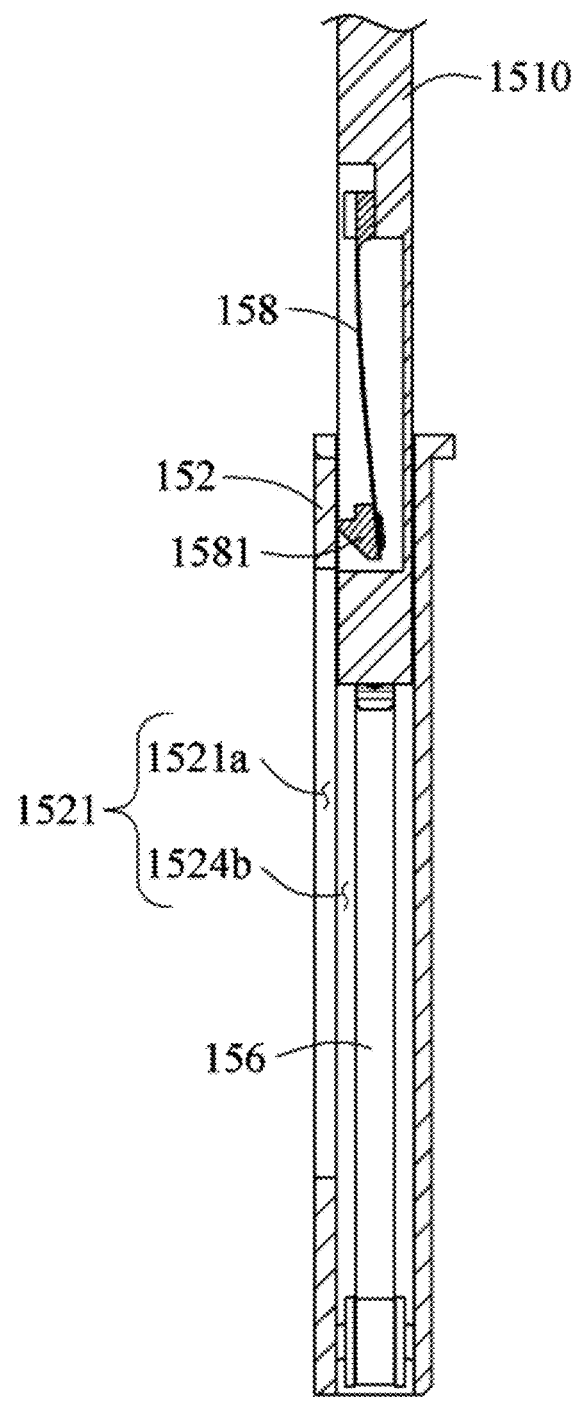
Figure 12C:
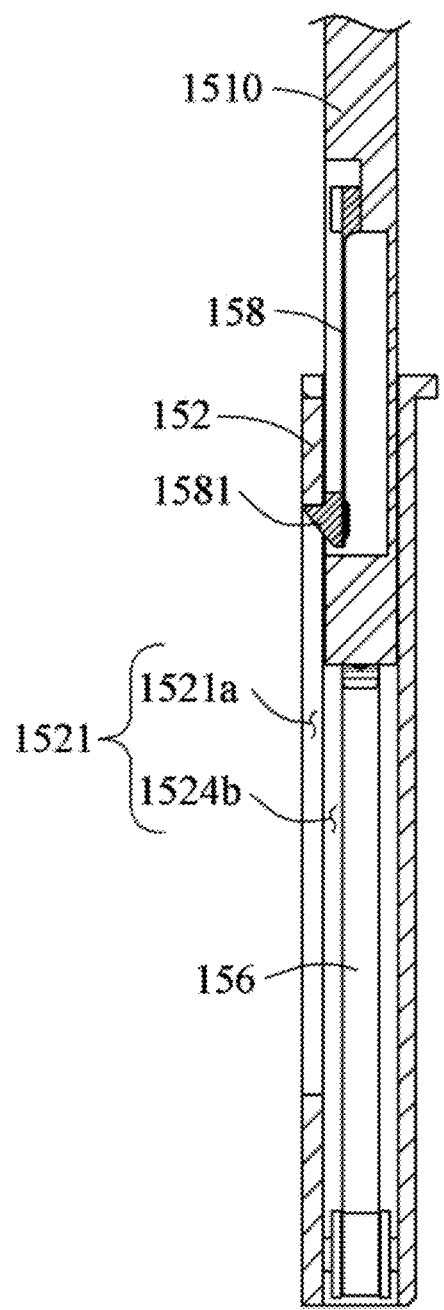

FIGS. 12A through 12C are cross-sectional views of the supporting module 15 illustrating an operation of the separation preventing member 158 according to example embodiments. In detail, FIGS. 12A through 12C illustrate a sequential process of coupling the sliding joint 151 to the supporting frame 152.

Referring to FIGS. 12A through 12C, the sliding space 1521 may include a hook moving space 1521a toward which the hook 1581 is to move, and a body moving space 1524b toward which the joint body 1510 is to slide.

In a state of FIG. 12A, when the sliding joint 151 is inserted into the supporting frame 152, the separation preventing member 158 may be elastically deformed, whereby the hook 1581 may be inserted into the sliding space 1521, as shown in FIG. 12B. The hook 1581 may be inserted into the hook moving space 1521a by an elastic restoring force, as shown in FIG. 12C. In a state of FIG. 12C, when the sliding joint 151 is drawn out from the supporting frame 152, the hook 1581 may be hung at an end portion of the hook moving space 1521a, whereby a separation of the sliding joint 151 from the supporting frame 152 may be prevented.

A user may separate the sliding joint 151 from the supporting frame 152 by drawing out the sliding joint 151 while sufficiently pressing the hook 1581. The hook 1581 may include a button portion configured to be readily pressed by the user. The button portion may include, for example, a urethane material.

Hereinafter, the same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 13:
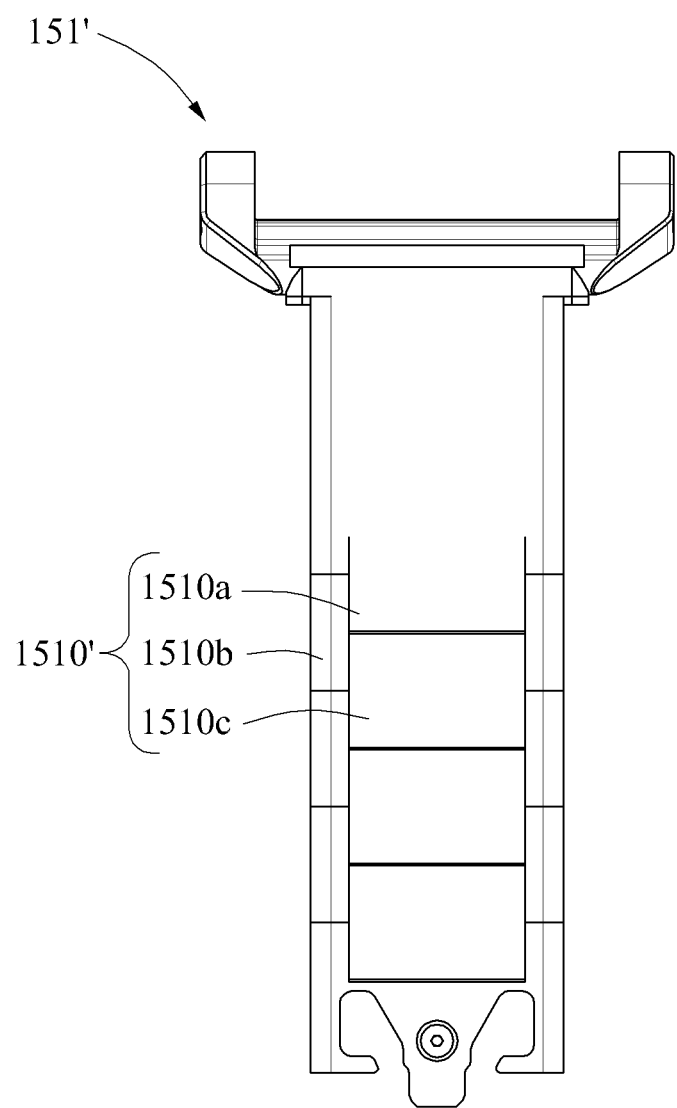
FIG. 13 is a perspective view of a sliding joint according to example embodiments.
Figure 14A:
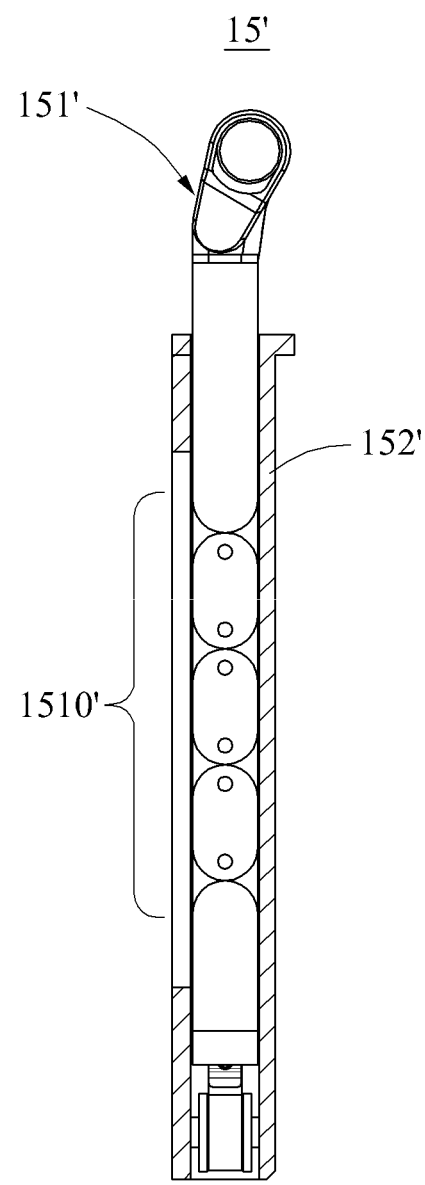
FIGS. 14A and 14B are views illustrating an operation of a supporting module according to example embodiments.
Figure 14B:
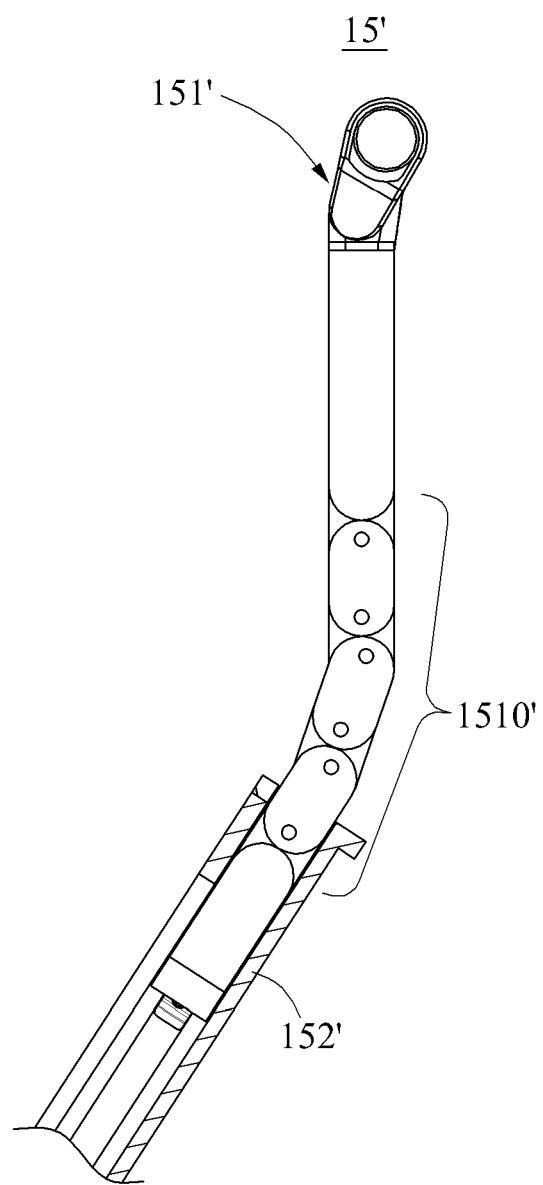

FIG. 13 is a perspective view of a sliding joint 151' according to example embodiments, and FIGS. 14A and 14B are views illustrating an operation of a supporting module 15' according to example embodiments.

Referring to FIGS. 13 through 14B, the supporting module 15' may include the sliding joint 151', and a supporting frame 152' into which the sliding joint 151' is to be slidingly inserted. The sliding joint 151' may include a joint body 1510'.

The joint body 1510' may include at least one sub-joint. The joint body 1510' may include a first sub-joint 1510a, a second sub-joint 1510b configured to rotate with respect to the first sub-joint 1510a, and a third sub-joint 1510c configured to rotate with respect to the second sub-joint 1510b. Rotation axes of the first sub-joint 1510a through the third sub-joint 1510c may be orthogonal to the rotation axis of the rotary joint 14 of FIG. 1. By the foregoing structure, rotation operations of the first sub-joint 1510a through the third sub-joint 1510c may prevent a waste of power to be transmitted from the rotary joint 14.

Figure 15:
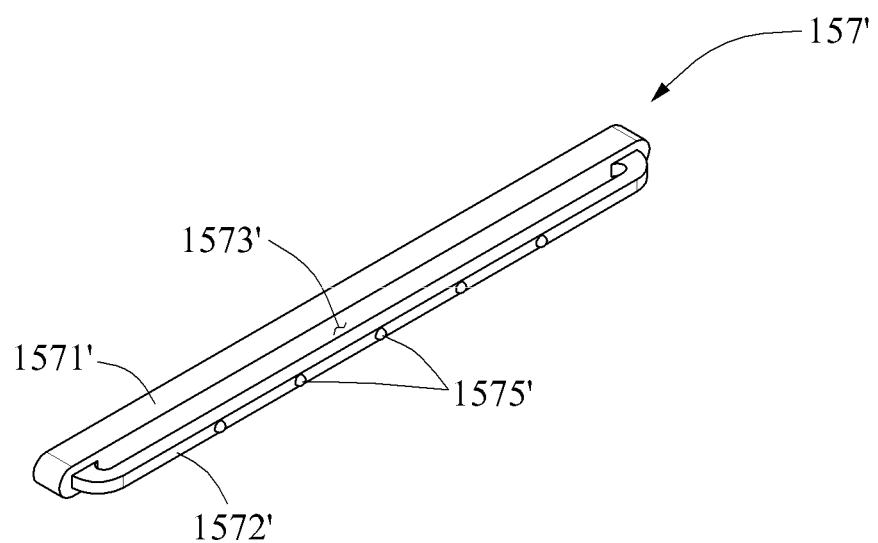
FIG. 15 is a perspective view of a gap preventing member according to example embodiments.

FIG. 15 is a perspective view of a gap preventing member 157' according to example embodiments.

Referring to FIG. 15, the gap preventing member 157' may include a fixing portion 1571', a rib 1572', a cushion space 1573', and at least one contact protrusion 1575'. The contact protrusion 1575' may protrude from the rib 1572'. A plurality of contact protrusions 1575' may be disposed to be spaced apart from each other at uniform intervals in a longitudinal direction of the rib 1572'. The contact protrusion 1575' may reduce a frictional force occurring between a sliding joint and a supporting frame.

Figure 16:
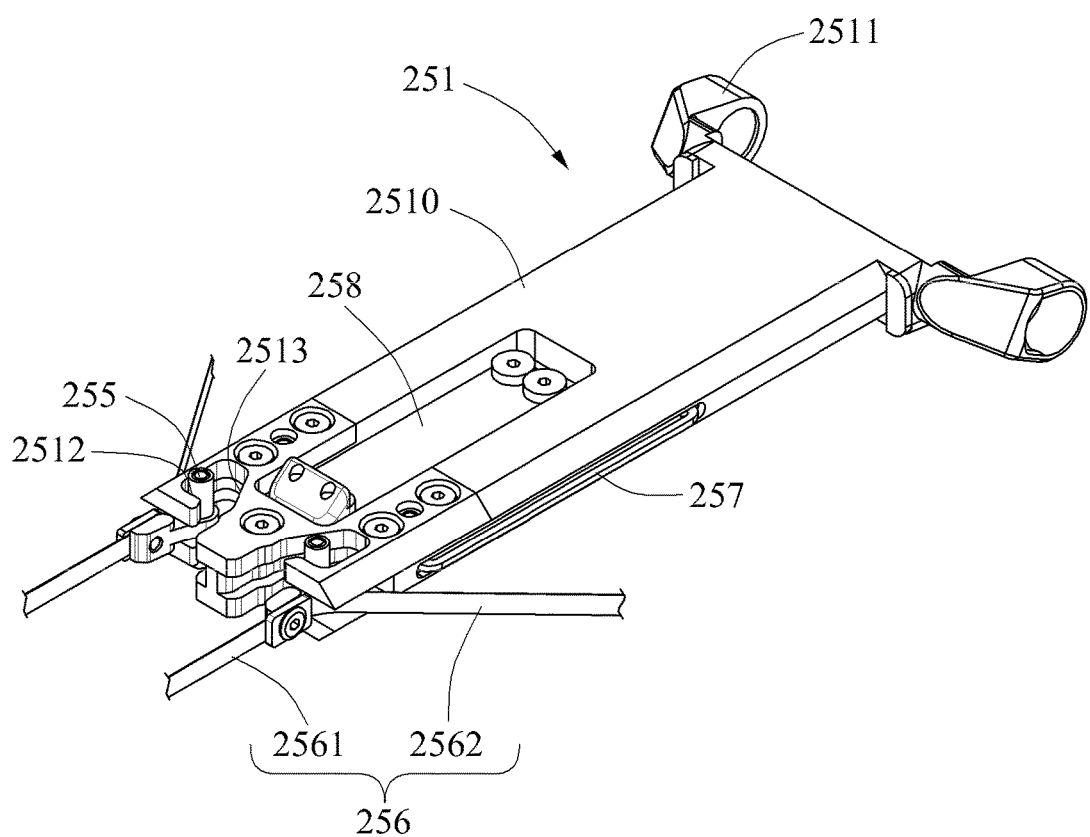
FIG. 16 is a view illustrating a sliding joint according to example embodiments.
Figure 17:
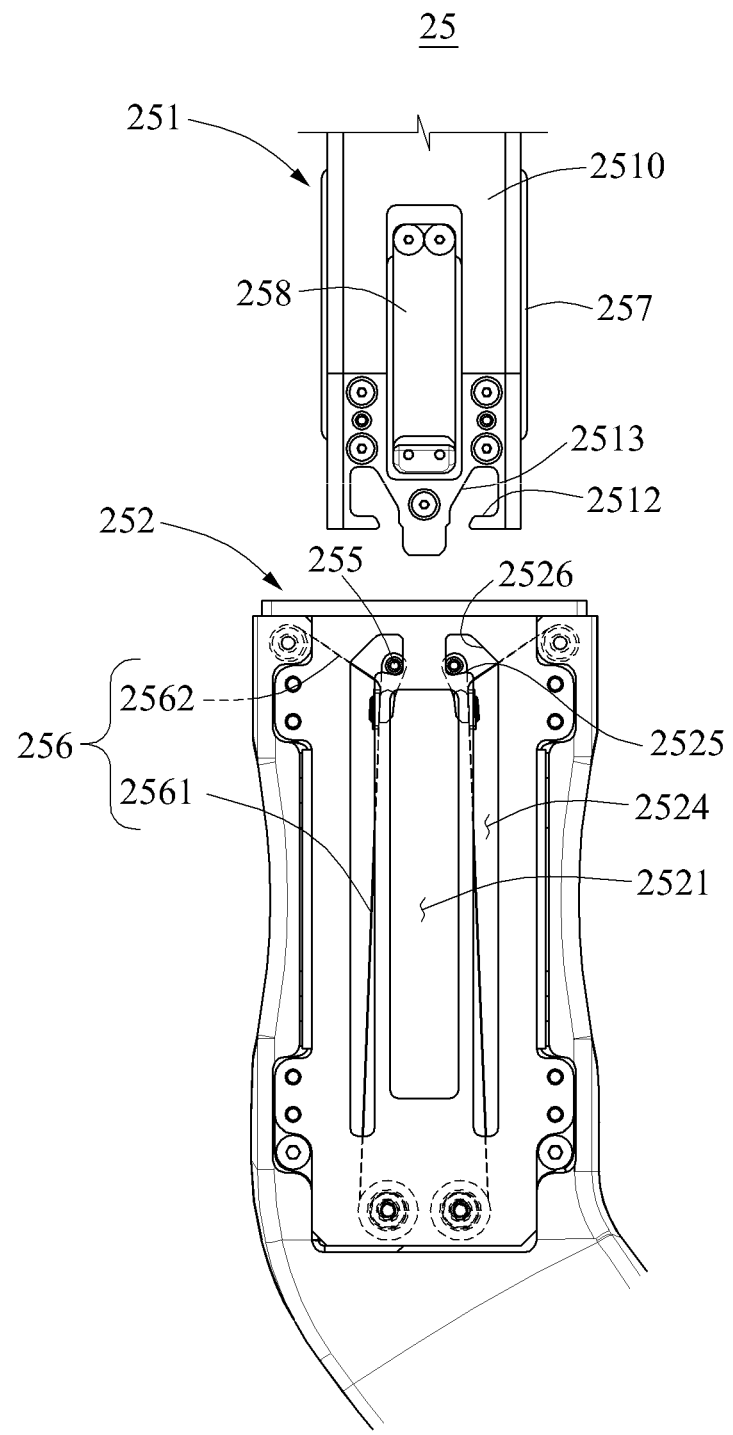
FIG. 17 is a view illustrating a sliding joint and a supporting frame being separated from each other according to example embodiments.
Figure 18:
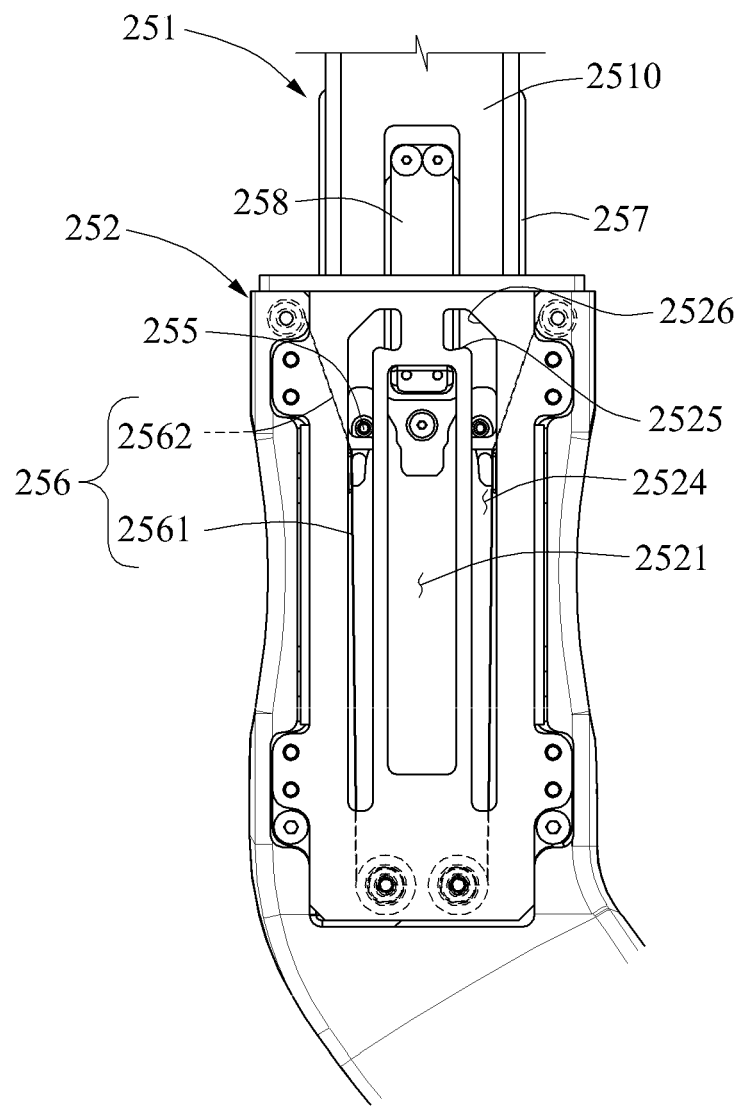
FIG. 18 is a view illustrating a sliding joint and a supporting frame being coupled to each other according to example embodiments.

FIG. 16 is a view illustrating a sliding joint 251 according to example embodiments, FIG. 17 is a view illustrating the sliding joint 251 and a supporting frame 252 being separated from each other according to example embodiments, and FIG. 18 is a view illustrating the sliding joint 251 and the supporting frame 252 being coupled to each other according to example embodiments.

Referring to FIGS. 16 through 18, a supporting module 25 may include the sliding joint 251, the supporting frame 252, a slider 255, an elastic module 256, a gap preventing member 257, and a separation preventing member 258.

The sliding joint 251 may include a joint body 2510, a hinge 2511, a hanging portion 2512, and a hanging guide 2513. The supporting frame 252 may include a sliding space 2521, a sliding guide 2524, a temporary fixing portion 2525, and a separation guide 2526.

The elastic module 256 may include a first elastic member 2561, and a second elastic member 2562. The first elastic member 2561 and the second elastic member 2562 may enable the sliding joint 251 to maintain neutrality at a desired (or, alternatively, a predetermined) position. In detail, in a state in which another external force is not applied to the sliding joint 251, the first elastic member 2561 and the second elastic member 2562 may apply forces to the sliding joint 251 in opposite directions. In further detail, one of the first elastic member 2561 and the second elastic member 2562 may provide an elastic force in a direction in which the sliding joint 251 is separated from the supporting frame 252, and the other of the first elastic member 2561 and the second elastic member 2562 may provide an elastic force in a direction in which the sliding joint 251 is inserted into the supporting frame 252.

For example, one side of the first elastic member 2561 may be fixed to the supporting frame 252, and another side of the first elastic member 2561 may be fixed to the slider 255. One side of the second elastic member 2562 may be fixed on an opposite side of the first elastic member 2561, and another side of the second elastic member 2562 may be fixed to the slider 255. The first elastic member 2561 and the second elastic member 2562 may apply forces to the slider 255 at a neutral position in opposite directions.

The first elastic member 2561 and the second elastic member 2562 may include members including an elastic material such as a constant force spring, a tensile spring, a compression spring, and a rubber band, for example.

Figure 19A:
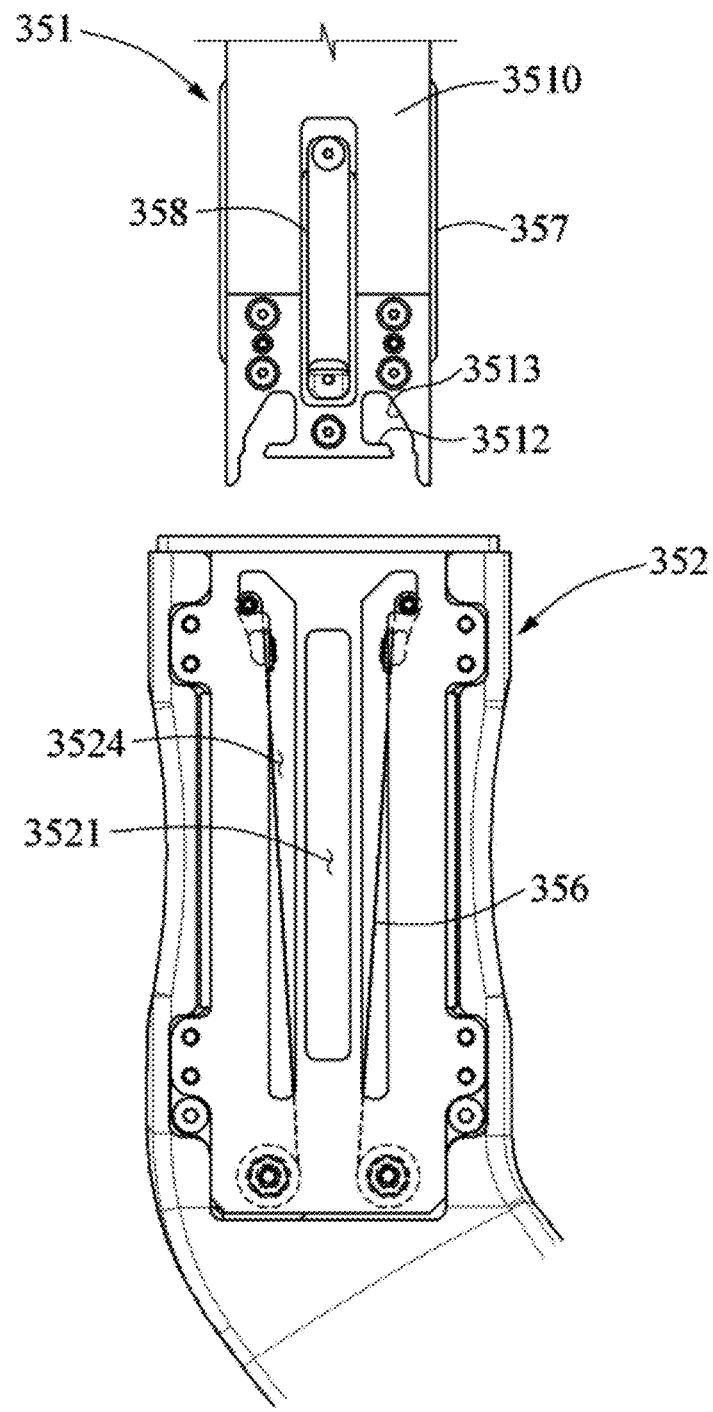
FIGS. 19A and 19B is a view illustrating a supporting module according to example embodiments.
Figure 19B:
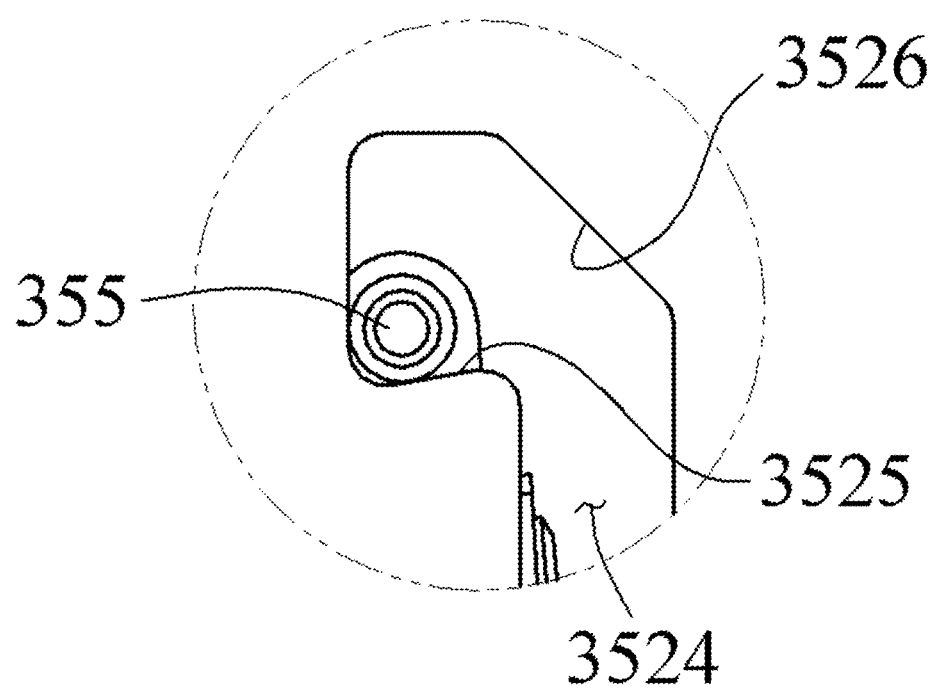

FIGS. 19A and 19B is a view illustrating a supporting module 35 according to example embodiments.

Referring to FIGS. 19A and 19B, the supporting module 35 may include a sliding joint 351, a supporting frame 352, a slider 355, an elastic module 356, a gap preventing member 357, and a separation preventing member 358.

The sliding joint 351 may include a joint body 3510, a hanging portion 3512, and a hanging guide 3513.

The slider 355 may be hung on the hanging portion 3512. For example, the hanging portion 3512 may protrude from a center of an end portion of the joint body 3510 toward an outer side. The hanging portion 3512 may be provided in a loop shape bent from an inner side of the joint body 3510 toward an outer side.

The hanging guide 3513 may guide the slider 355 to the hanging portion 3512. The hanging guide 3513 may be disposed to be spaced apart from the hanging portion 3512, whereby the slider 355 may be inserted into a space formed between the hanging portion 3512 and the hanging guide 3513. The hanging guide 3513 may be inclined upward in a direction of the hanging portion 3512, as illustrated in FIGS. 19A and 19B. In detail, the hanging guide 3513 may be inclined toward the hanging portion 3512 in a direction in which the sliding joint 351 is separated from the supporting frame 352.

The supporting frame 352 may include a sliding space 3521, a sliding guide 3524, a temporary fixing portion 3525, and a separation guide 3526.

The temporary fixing portion 3525 may temporarily fix the slider 355. The temporary fixing portion 3525 may be recessed from the sliding guide 3524. The temporary fixing portion 3525 may be recessed toward an outer side, as illustrated in FIGS. 19A and 19B. The temporary fixing portion 3525 may overlap the hanging guide 3513, when viewed from a coupling direction of the sliding joint 351 and the supporting frame 352. The temporary fixing portion 3525 may be inclined downward in a direction of an end portion, as illustrated in FIGS. 19A and 19B. In detail, the temporary fixing portion 3525 may be inclined in a direction in which the sliding joint 351 is coupled to the supporting frame 352. By the foregoing structure, although an elastic force of the elastic module 356 is applied to the slider 355, the slider 355 may be stably received in the temporary fixing portion 3525.

The separation guide 3526 may guide the slider 355 to the temporary fixing portion 3525. The separation guide 3526 may extend to be inclined from the sliding guide 3524. The separation guide 3526 may be inclined upward in a direction of an outer side, as illustrated in FIGS. 19A and 19B. In detail, the separation guide 3526 may be inclined toward the temporary fixing portion 3525 in a direction in which the sliding joint 351 is separated from the supporting frame 352.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A supporting module comprising:
a supporting frame having a sliding guide therein;
a slider configured to slide in the sliding guide;
a sliding joint configured to detachably couple to the slider based on a relative moving direction of the sliding joint with respect to the supporting frame; and
an elastic module associated with the supporting frame, the elastic module configured to provide an elastic force to the sliding joint,
wherein the supporting frame includes a temporary fixing portion recessed from the sliding guide, the temporary fixing portion configured to temporarily fix the slider therein such that the slider does not slide in the sliding guide.

2. The supporting module of claim 1, wherein the elastic module comprises:
a constant force spring configured to provide a constant force to the sliding joint irrespective of a change in a position of the sliding joint as the sliding joint slides along the sliding guide.

3. The supporting module of claim 1, wherein the elastic module is configured to position the sliding joint at a center of the sliding guide by providing the elastic force thereto.

4. The supporting module of claim 1, wherein the elastic module comprises:
a first elastic member and a second elastic member configured to apply a plurality of elastic forces to the sliding joint in opposite directions when an external force is not applied to the sliding joint.

5. The supporting module of claim 1, wherein the sliding joint comprises:
a joint body configured detachably couple to the supporting frame; and
a hanging portion extending from one side of the joint body, wherein
the slider is configured to hang on the hanging portion.

6. The supporting module of claim 5, wherein
the slider is configured to hang on the hanging portion when the joint body is coupled to the supporting frame, and
the slider is configured to separate from the hanging portion when the joint body is separated from the supporting frame.

7. The supporting module of claim 1, wherein the sliding joint further comprises:
a hanging guide opposite the hanging portion on a joint body, the hanging guide configured to guide the slider from the temporary fixing portion to the sliding guide when the sliding joint is inserted in the supporting frame.

8. The supporting module of claim 7, wherein
the temporary fixing portion is inclined at a first slope from the sliding guide toward an insertion direction of the sliding joint, and the hanging guide is inclined at a second slope from the sliding guide toward the insertion direction of the sliding joint, the second slope being a steeper slope than the first slope.

9. A supporting module comprising:

a supporting frame having a sliding guide therein;

a slider configured to slide in the sliding guide; and a sliding joint configured to detachably couple to the slider based on a relative moving direction of the sliding joint with respect to the supporting frame, wherein the supporting frame has a sliding space therein such that the sliding space has a larger cross-sectional area than the sliding joint and the sliding joint is configured to penetrate the sliding space, and the supporting frame includes a gap preventing member between an inner wall of the supporting frame and the sliding joint.

10. The supporting module of claim 9, wherein the sliding joint comprises:

a joint body configured to detachable couple to the supporting frame; and a hanging portion extending from one side of the joint body, wherein the sliding joint is configured to detachably couple to the slider via engagement of the hanging portion and the slider.

11. The supporting module of claim 10, wherein the slider is configured to hang on the hanging portion when the joint body is inserted into the supporting frame by a length greater than or equal to a first set length.

12. The supporting module of claim 10, wherein the slider is configured to separate from the hanging portion when the joint body is drawn out from the supporting frame by a length greater than or equal to a second set length.

13. The supporting module of claim 12, wherein the supporting frame further comprises:

a separation guide extending from a top end of the sliding guide, the separation guide configured to guide the slider when the slider separates from the hanging portion.

14. The supporting module of claim 13, wherein the separation guide is inclined from the sliding guide toward a drawing-out direction of the sliding joint.

15. The supporting module of claim 9, wherein supporting frame is shaped such that an end portion of the sliding space is configured to have a smaller cross-sectional area than a central portion thereof, and the gap preventing member comprises:

a fixing portion associated with the sliding joint; and a rib configured to protrude from the fixing portion such that the rib is in contact with the inner wall of the supporting frame.

16. The supporting module of claim 9, further comprising:

a separation preventing member associated with one of the supporting frame and the sliding joint, the separation preventing member configured to restrict a maximum length by which the sliding joint is drawable from the supporting frame.

17. The supporting module of claim 9, wherein the sliding joint comprises:

a sliding body having a plurality of joints therein.

\* \* \* \* \*